(12) United States Patent
Rudy

(10) Patent No.: US 6,772,004 B2
(45) Date of Patent: Aug. 3, 2004

(54) SYSTEM AND METHOD FOR NON-INVASIVE ELECTROCARDIOGRAPHIC IMAGING

(75) Inventor: Yoram Rudy, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 455 days.

(21) Appl. No.: 10/037,603

(22) Filed: Oct. 19, 2001

(65) Prior Publication Data

US 2002/0128565 A1 Sep. 12, 2002

Related U.S. Application Data

(63) Continuation of application No. 09/463,428, filed as application No. PCT/US98/15927 on Jul. 29, 1998, now abandoned.
(60) Provisional application No. 60/054,342, filed on Jul. 31, 1997.

(51) Int. Cl.$^7$ ................................................ A61B 5/044
(52) U.S. Cl. ........................ 600/509; 600/523; 600/411
(58) Field of Search ................................ 600/509, 513, 600/483, 523, 411, 427, 389, 416, 382, 386, 393; 128/920

(56) References Cited

U.S. PATENT DOCUMENTS

| | | | |
|---|---|---|---|
| 3,848,582 A | 11/1974 | Milani et al. | |
| 3,858,576 A | 1/1975 | Dehnert et al. | |
| 4,033,336 A | 7/1977 | Murawski et al. | |
| 4,183,354 A | 1/1980 | Sibley et al. | |
| 4,203,451 A | 5/1980 | Panico | |
| 4,535,783 A | 8/1985 | Marangoni | |
| 4,593,698 A | 6/1986 | Athans | |
| 4,606,352 A | 8/1986 | Geddes et al. | |
| 4,805,631 A | 2/1989 | Roi du Maroc, II. | |

(List continued on next page.)

OTHER PUBLICATIONS

Burnes, JE, Taccardi, B., Rudy, Y., "A Noninvasive Imaging Modality for Cardiac Arrhythmias", *Circulation*, vol. 102, No. 17, Oct. 24, 2000, pp. 2152–2158.

Ramanathan, C., Rudy, Y., "Electrocardiographic Imaging: I. Effect of Torso Inhomogeneities on Body Surface Electrocardiographic Potentials", *Journal of Cardiovascular Electrophysiology*, vol. 12, No. 2, Feb. 2001, pp. 229–240.

Ramanathan, C., Rudy, Y., "Electrocardiographic Imaging: II. Effect of Torso Inhomogeneities on Noninvasive Reconstruction of Epicardial Potentials, Electrograms, and Isochrones", Journal of Cardiovascular Electrophysiology, vol. 12, No. 2, Feb. 2001, pp. 241–252.

Burnes, JE., Ghanem, RN., Waldo, AL., Rudy, Y., "Imaging Dispersion of Myocardial Repolarization, I. Comparison of Body–Surface and Epicardial Measures", *Circulation*, vol. 104, No. 11, Sep. 11, 2001, pp. 1299–1305.

(List continued on next page.)

*Primary Examiner*—Kennedy Schaetzle
(74) *Attorney, Agent, or Firm*—Kevin A. Oliver; Foley Hoag LLP

(57) ABSTRACT

A system and method is provided for non-invasively determining electrical activity of the heart of a human being. Electrical potentials are measured on the body surface via an electrode vest (12), and a body surface potential map is generated. A matrix of transformation based on the geometry of the torso, the heart, locations of electrodes, and position of the heart within the torso is also determined with the aid of a processor (24), and a geometry determining device (26). The electrical potential distribution over the epicardial surface of the heart is then determined based on a regularized matrix of transformation, and the body surface potential map. Using the epicardial potential distributions, epicardial electrogram, isochronal are also reconstructed, and displayed via an output device (28).

17 Claims, 31 Drawing Sheets

| | | |
|---|---|---|
| 4,858,617 A | 8/1989 | Sanders |

U.S. PATENT DOCUMENTS

| | | | |
|---|---|---|---|
| 4,949,725 A | 8/1990 | Raviv et al. | 128/731 |
| 4,989,611 A | 2/1991 | Zanetti et al. | |
| 4,991,580 A | 2/1991 | Moore | |
| 4,991,587 A | 2/1991 | Blakeley et al. | |
| 5,020,540 A | 6/1991 | Chamoun | |
| 5,038,791 A | 8/1991 | Collins et al. | 128/696 |
| 5,042,499 A | 8/1991 | Frank et al. | |
| 5,086,776 A | 2/1992 | Fowler, Jr. et al. | |
| 5,151,856 A | 9/1992 | Halmann et al. | 364/413.03 |
| 5,161,539 A | 11/1992 | Evans et al. | |
| 5,205,295 A | 4/1993 | Del Mar et al. | |
| 5,263,488 A | 11/1993 | Van Veen et al. | 128/731 |
| 5,311,867 A | 5/1994 | Kynor | |
| 5,311,873 A | 5/1994 | Savard et al. | |
| 5,343,870 A | 9/1994 | Gallant et al. | |
| 5,433,198 A | 7/1995 | Desai | |
| 5,433,209 A | 7/1995 | Gallant et al. | |
| 5,483,968 A * | 1/1996 | Adam et al. | 600/508 |
| 5,487,391 A | 1/1996 | Panescu | |
| 5,503,149 A | 4/1996 | Beavin | |
| 5,503,158 A | 4/1996 | Coppock et al. | |
| 5,568,809 A | 10/1996 | Ben-haim | |
| 5,606,978 A | 3/1997 | Armstrong et al. | |
| 5,687,737 A * | 11/1997 | Branham et al. | 600/523 |
| 5,947,899 A | 9/1999 | Winslow et al. | 600/410 |
| 6,014,582 A | 1/2000 | He | 600/544 |
| 6,052,618 A | 4/2000 | Dahlke et al. | 600/523 |
| 6,236,886 B1 | 5/2001 | Cherepenin et al. | 600/547 |

OTHER PUBLICATIONS

Burnes, JE., Ghanem, RN., Waldo, AL., Rudy, Y., "Imaging Dispersion of Myocardial Repolarization, II. Noninvasive Reconstruction of Epicardial Measures", *Circulation*, vol. 104, No. 11, Sep. 11, 2001, pp. 1306–1312.

Ghanem, RN., Burnes, JE., Waldo, AL., Rudy, Y., "Electrocardiographic Imaging: Noninvasive Reconstruction of Epicardial Measures of Dispersion of Repolarization", Biomedizinische Technik, vol. 46, Suppl.. vol. 2, 2001, pp. 201–203.

Burnes, JE., Taccardi, B., Ershler, PR., Rudy, Y., "Noninvasive ECG Imaging of Substrate and Intramural Ventricular Tachycardia in Infarcted Hearts", *Journal of the American College of Cardiology*, Dec., 2001, in press.

Tikhonov, A.N., Arsenin, V.Y., "Solutions of Ill–Posed Problems", Chapter II. "The Regularization Method", 1977 V.H. Winston & Sons, Washington, D.C., A Halsted Press , John Wiley & Sons, pp. 45–62.

Brebbia, C.A., Telles, J.C.F., Wrobel, L.C., "Boundary Element Techniques—Theory and Applications in Engineering", Springer–Verlag, 1984, pp. 127–137.

Brebbia, C.A., J. Dominguez, "Boundary Elements, An Introductory Course", Computational Mechanics Publications, Southampton, Boston, pp. 87–90.

Jackson, J.D., "Classical Electrodynamics", Second Edition, John Wiley & Sons, pp. 39–43.

Rudy Y, Messinger–Rapport BJ, The inverse problem in electrocardiography solutions in terms of epicardial potentials,: *CRC Crit Rev Biomed Eng.*, 16:215–268 (1988).

Rudy Y, Oster HS, "The electrocardiographic inverse problem, " *CRC Crit Rev Biomed Eng.*, 20:25–46 (1992).

Messinger–Rapport BJ, Rudy Y, "Computational issues of importance to the inverse recovery of epicardial potentials in a realistic heart–torso geometry," *Math Biosci*, 97:85–120 (1989) (published erratum in *Math Biosci*, 99(1):141 (Apr. 1990)).

Oster HS, Rudy Y, "The use of temporal information in the regularization of the inverse problem of a electrocardiography," *IEEE Trans Biomed Eng.*, 39:65–75 (1992).

Messinger, Rapport BJ, Rudy Y, "Regularization of the inverse problem in electrocardiography. A model study," *Math Biosci*, 89:79–118 (1988).

Colli–Franzone P., Guerri L., Taccardi B., Viganotti C., "Mathematical procedure for solving the inverse problem of electrocardiography," *Math Biosci*, 77:353–96 (1985).

Colli–Franzone P., Guerri L., Taccardi B., Viganotti C., "Finite element approximation of regularized solutions of the inverse potential problem of electrocardiography and applications to experimental data", Calcolo 1985, 22:91–186.

Taccardi, Macchi, "Effect of myocardial fiber direction on epicardial potentials," *Circulation*, 90:3076–90 (1994).

Rudy, Y., Burnes, J.E., "Noninvasive Electrocardiographic Imaging," *Annals of Noninvasive Electrocardiology*, vol. 4, No. 3, Jul. 1999 (Futura Publishing Company, Inc., Armonk, NY).

Oster, H.S., Taccardi, B., Lux, R.L., Ershler, P.R., Rudy, Y., "Noninvasive Electrocardiographic Imaging—Reconstruction of Epicardial Potentials, Electrograms, and Isochrones and Localization of Single and Multiple Electrocardiac Events", *Circulation*, vol. 96, No. 3, Aug. 5, 1997.

Oster, H.S., Taccardi, B., Lux, R.L., Ershler, P.R., Rudy, Y., "Electrocardiographic Imaging—Noninvasive Characterization of Intramural Myocardial Activation From Inverse–Reconstructed Epicardial Potentials and Electrograms", *Circulation*, 1998;97, Apr. 21, 1998, pp. 1496–1507.

Burnes, J.E., Taccardi, B., MacLeod, R.S., Rudy, Y., "Noninvasive ECG Imaging of Electrophysiologically Abnormal Substrates inInfarcted Hearts—A Model Study", *Circulation*, 2000;101,Feb. 8, 2000, pp. 533–540.

Rudy Y, Taccardi B, Noninvasive Imaging and Catheter Imaging of Potentials, Electrograms, and Isochrones on the Ventricular Surfaces, *Journal of Electrocardiology*, vol. 30 Supplement, (1998) pp. 19–23.

Oster HS, Rudy Y, "Regional Regularization of the Electrocardiographic Inverse Problem: A Model Study Using Spherical Geometry", *IEEE Transactions on Biomedical Engineering*, vol. 44, No. 2, Feb. 1997, pp. 188–199.

Burnes JE, Kaelber DC, Taccardi B, Lux RL, Ershler PH, Rudy Y, "A field–Compatible Method For Interpolating Biopotentials", *Annals of Biomedical Engineering*, vol. 26, pp. 37–47, 1998.

* cited by examiner

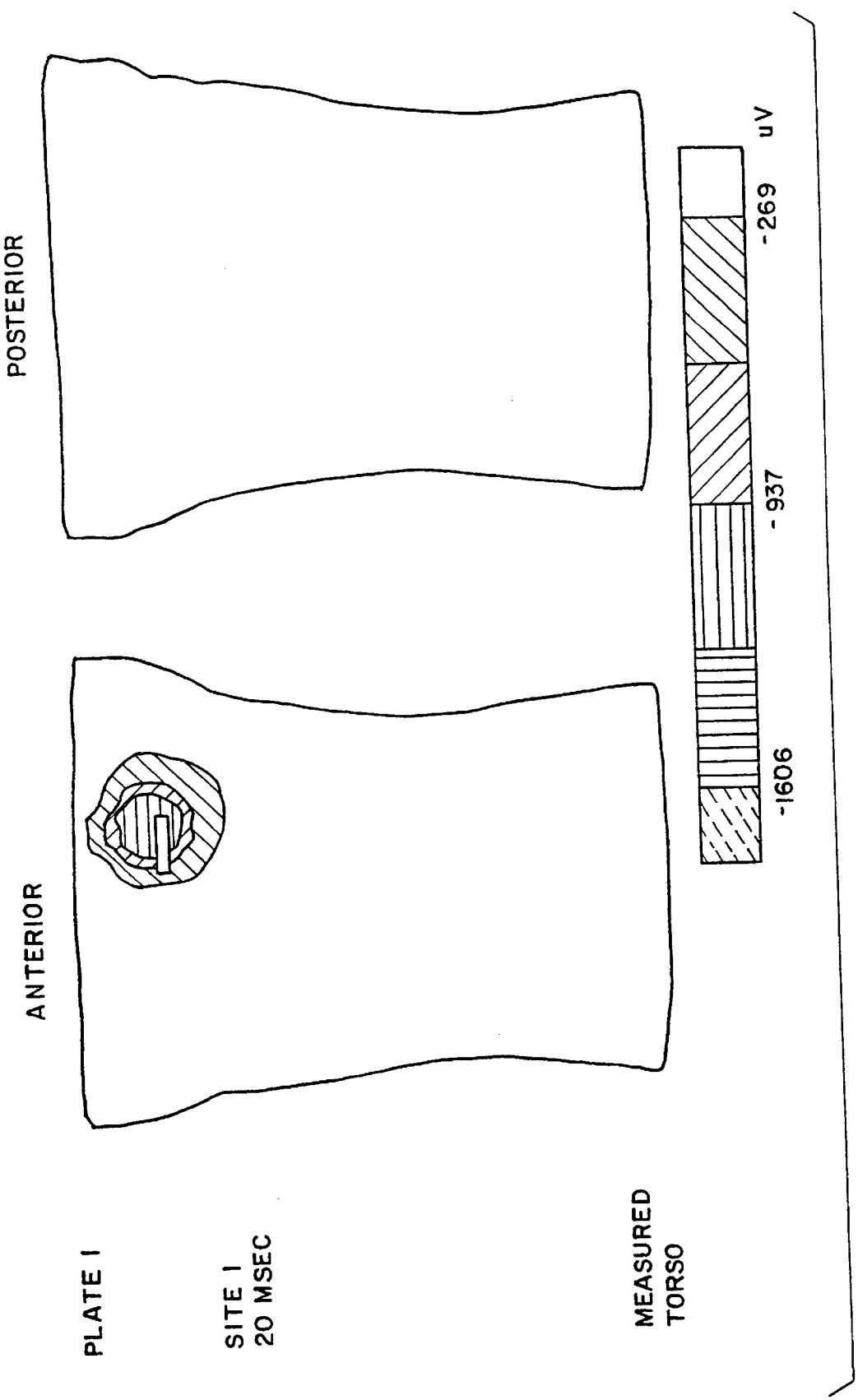

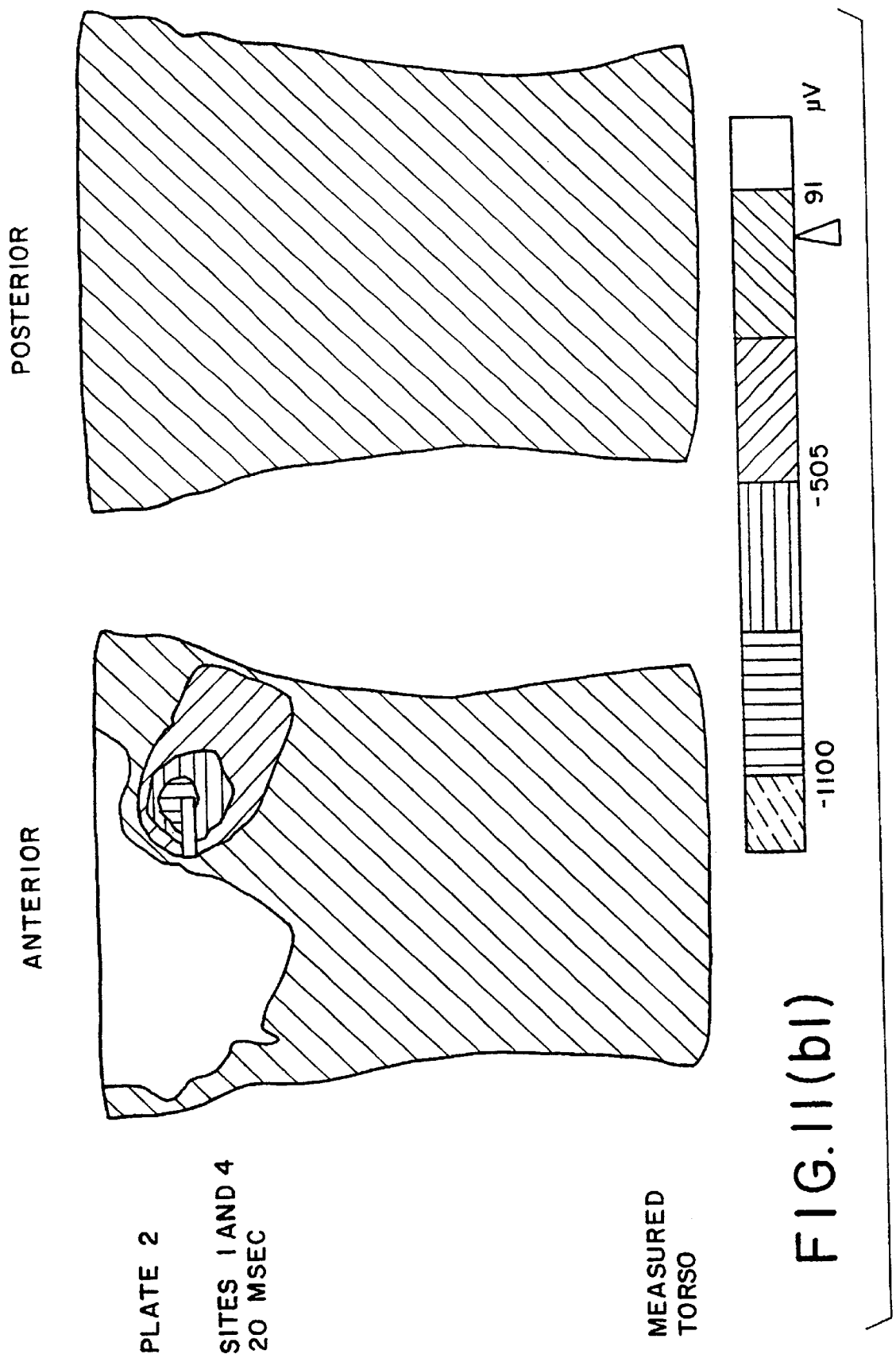

ALL SITES
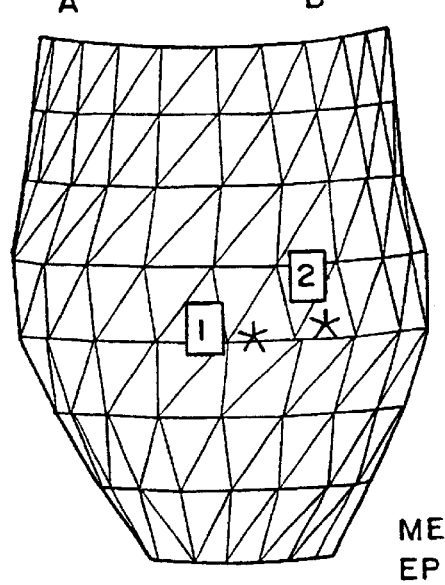
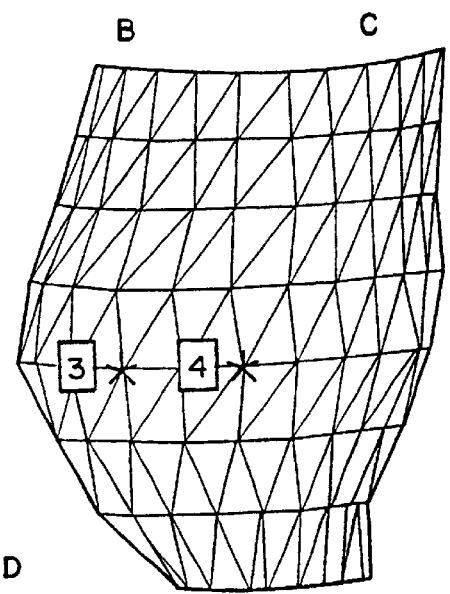
MEASURED EPICARDIUM
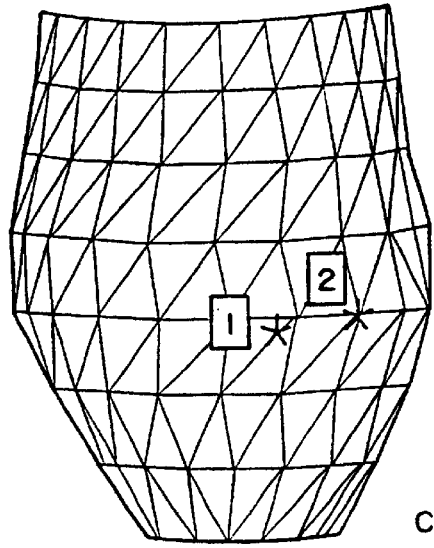
COMPUTED EPICARDIUM
FIG. 14

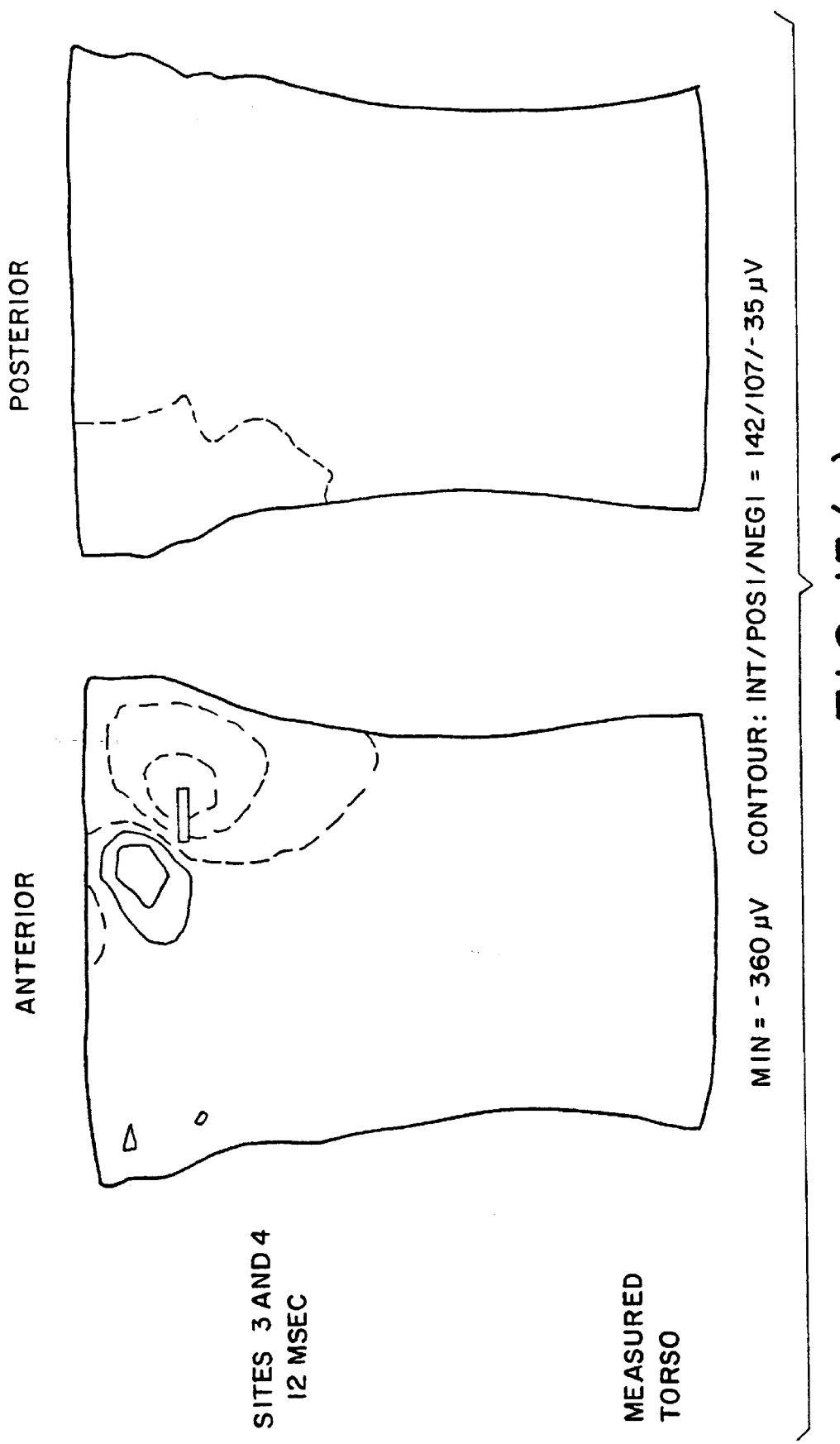

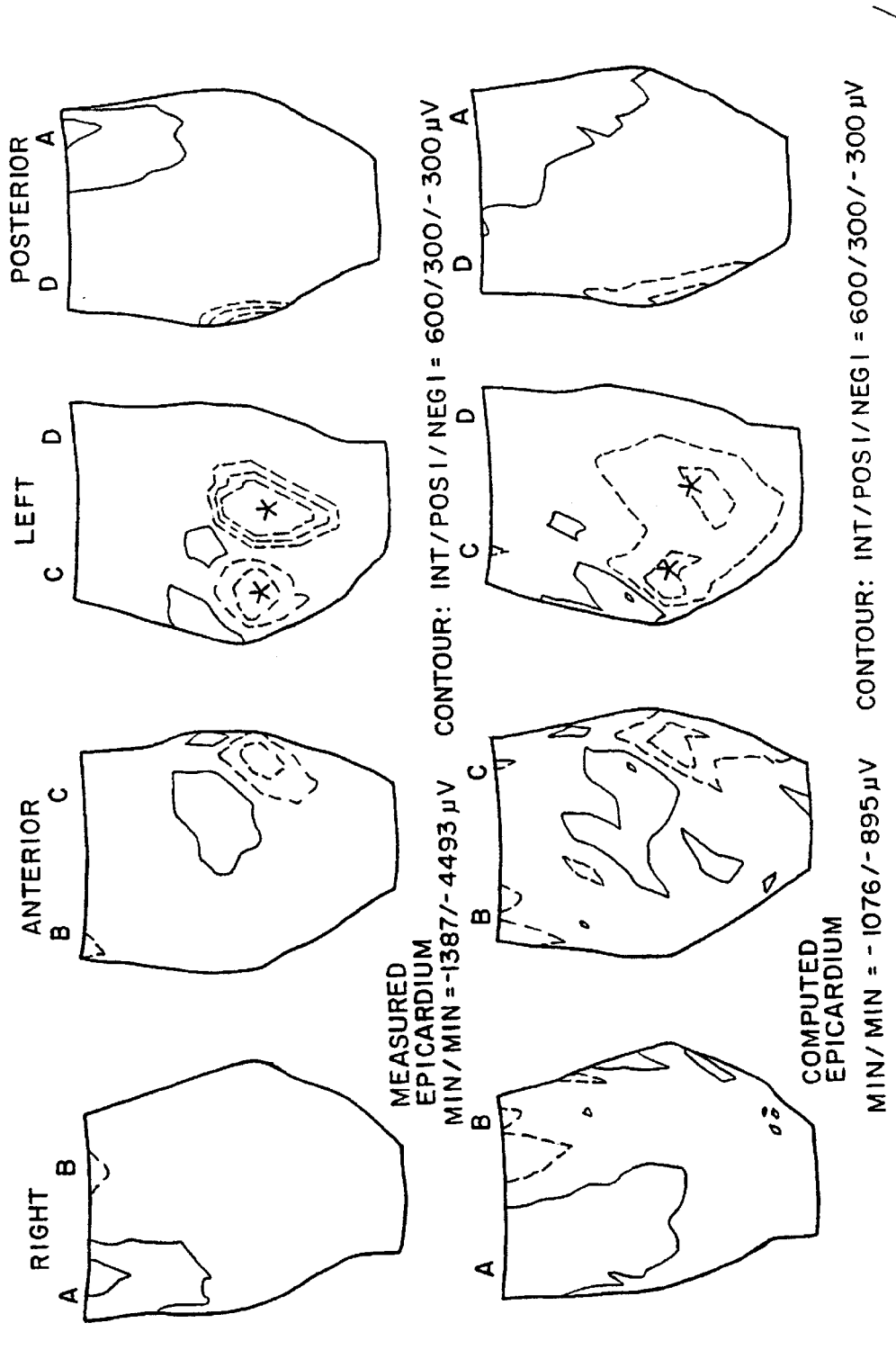

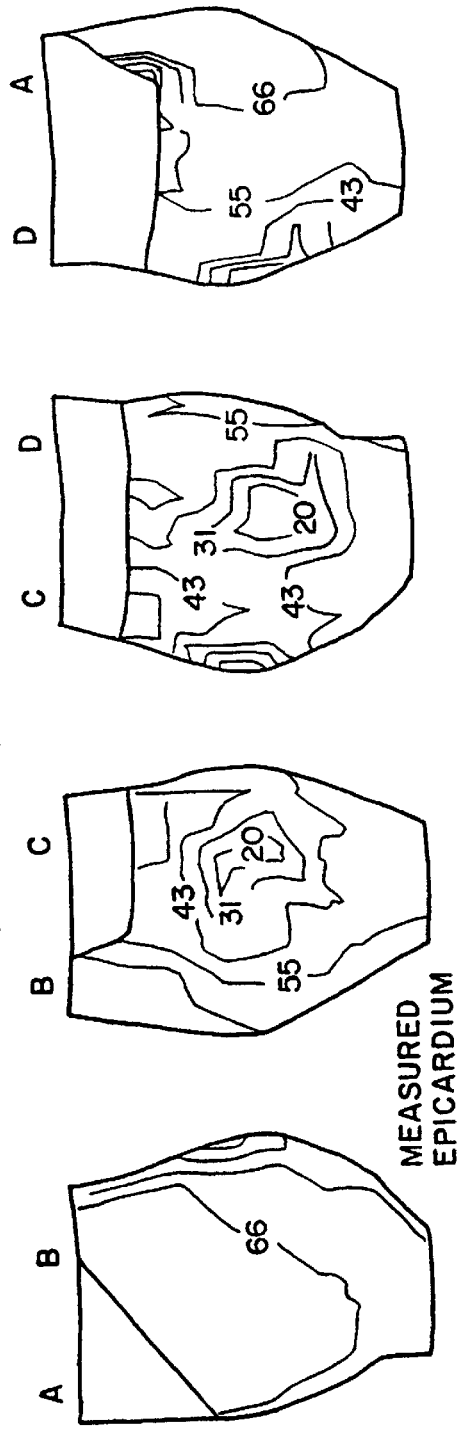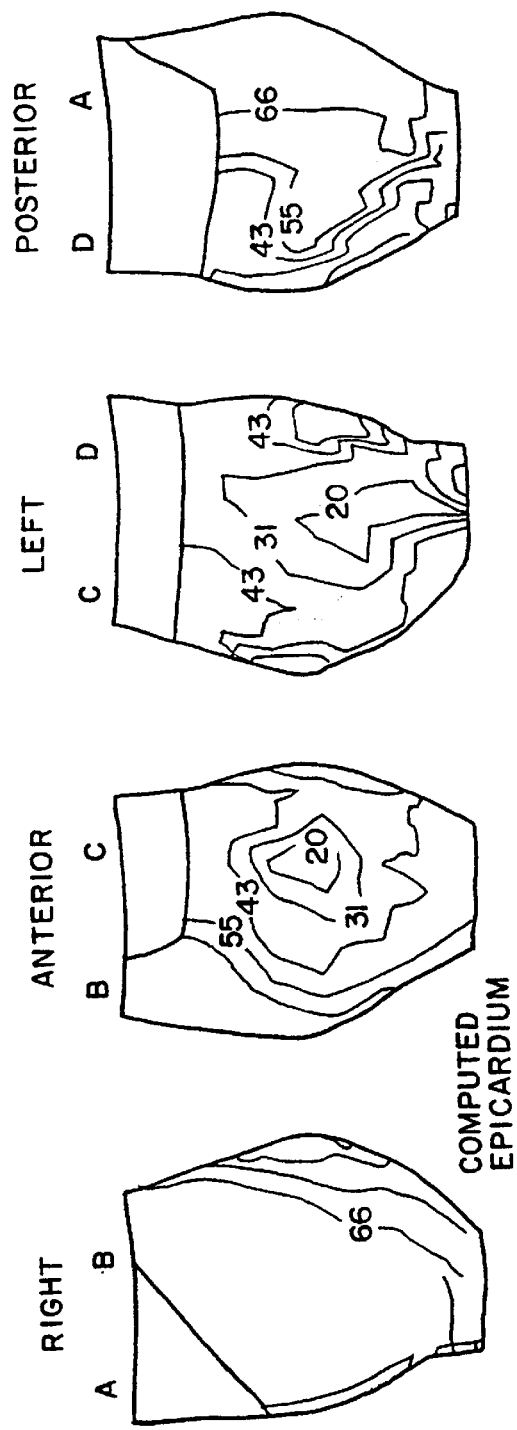
FIG. 18

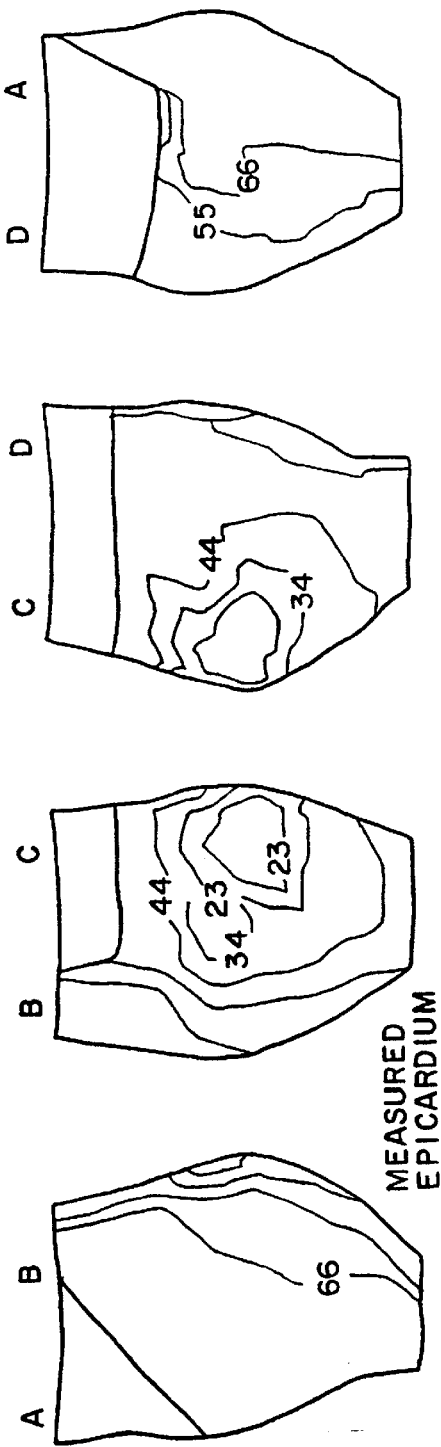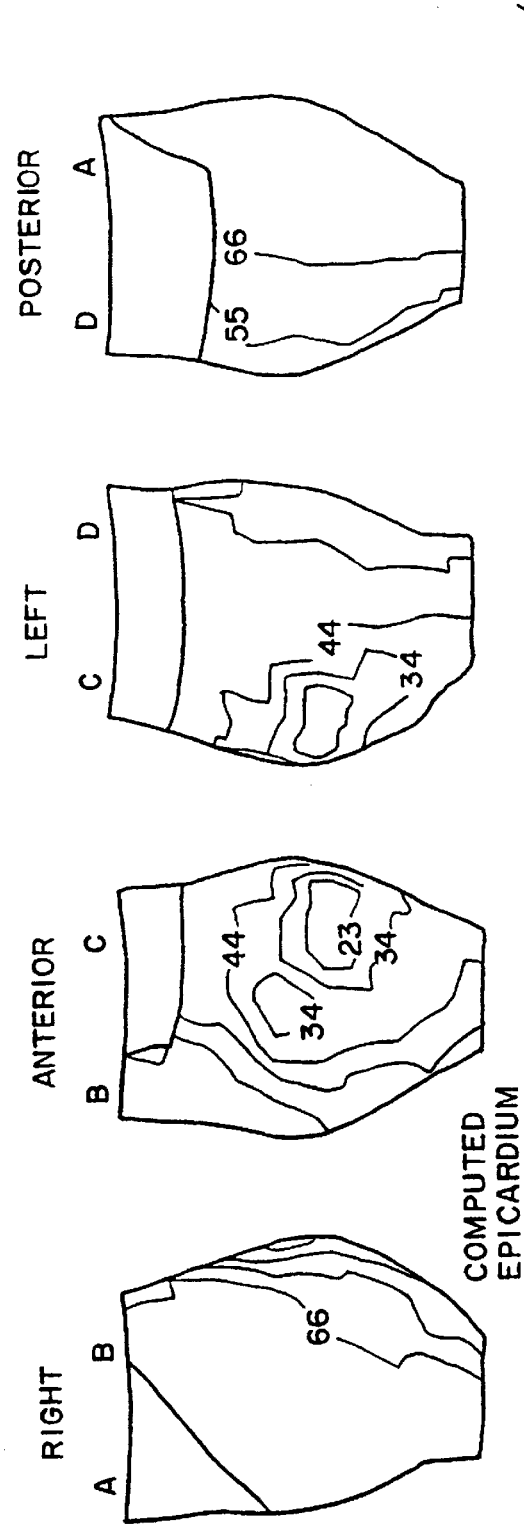
FIG. 19

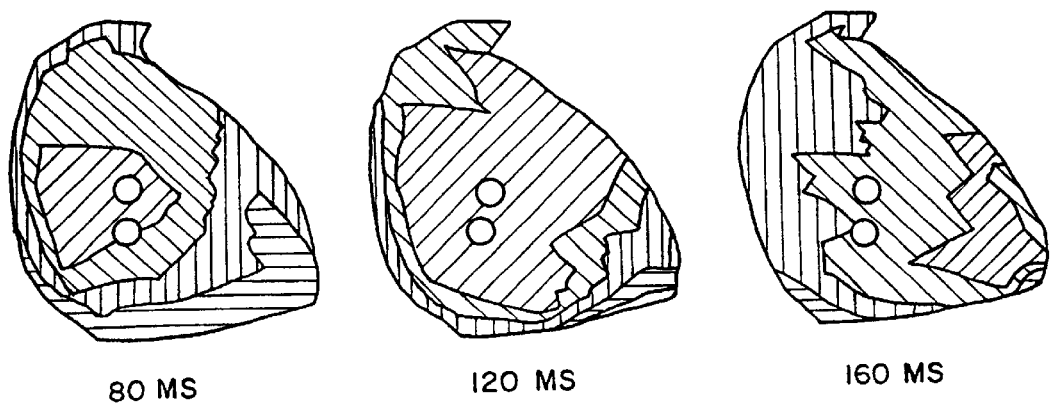
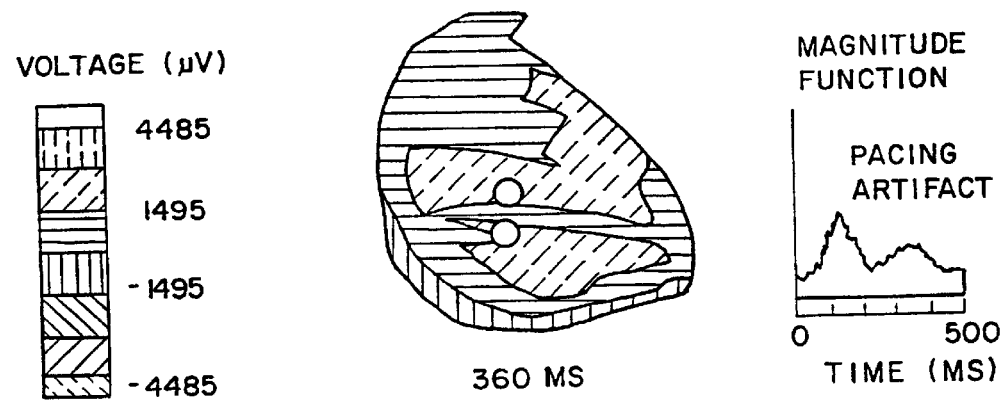
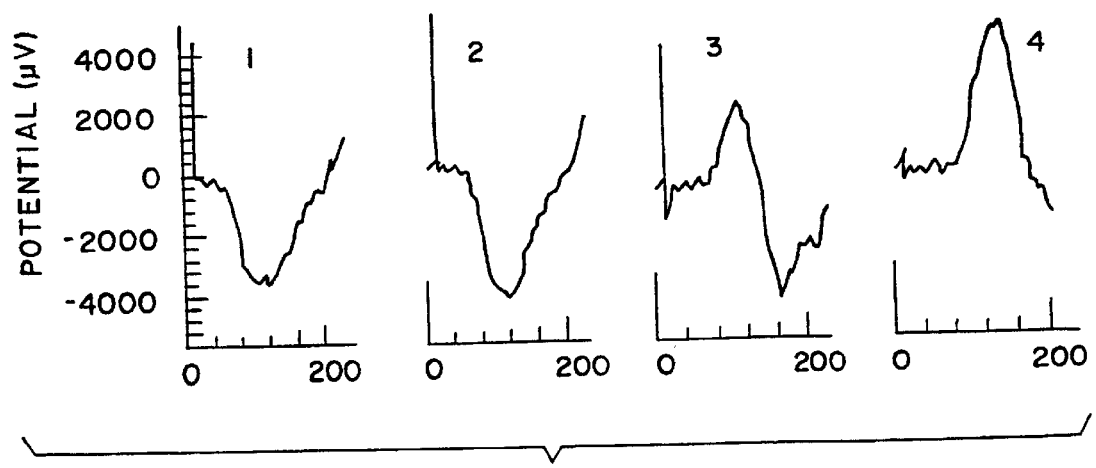
FIG. 21

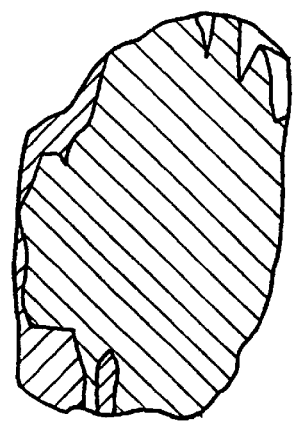
24 MS
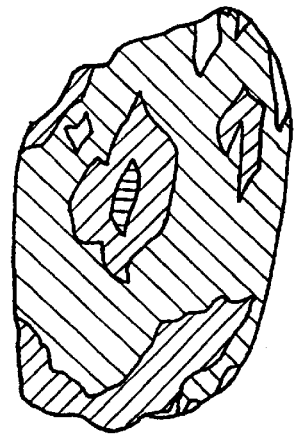
28 MS
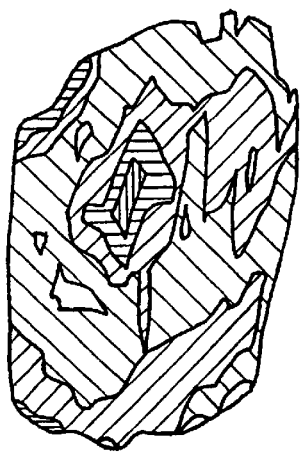
32 MS
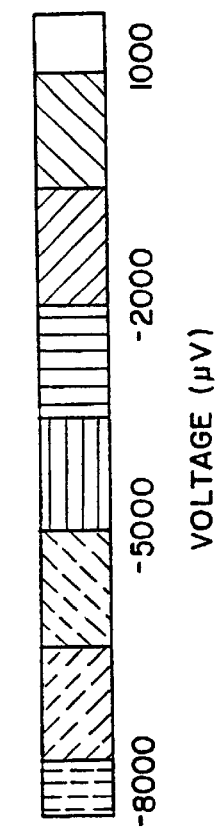
VOLTAGE (μV)
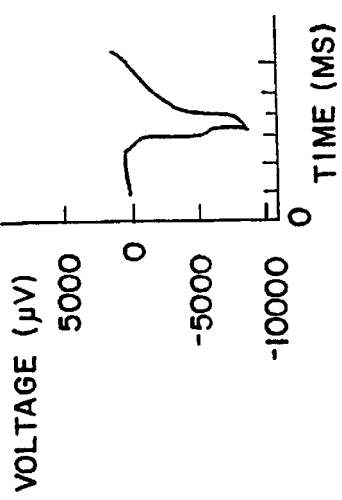
FIG. 22

SYSTEM AND METHOD FOR NON-INVASIVE ELECTROCARDIOGRAPHIC IMAGING

This application is a continuation application of U.S. patent application Ser. No. 09/463,428 (filed Mar. 29, 2000), now abandoned which is based on International Application No. PCT/US98/15927, filed Jul. 29, 1998 (having International Publication No. WO99/05962 and an International Publication Date of Feb. 11, 1999), which claims priority to U.S. Provisional Application No. 60/054,342 (filed Jul. 31, 1997).

ACKNOWLEDGMENTS

This research is supported by the National Institutes of Health, Grant No. 2 RO1 HL-33343 (Sponsor: NIH-NHLBI).

BACKGROUND OF THE INVENTION

This invention relates to a system and method for non-invasive electrocardiographic imaging ("ECGI"). More particularly, the invention is directed to a system and method using recorded body surface potentials that are noninvasively obtained and combined with data representing the geometry of a body torso to generate electrocardiographic images representing electrical activity of the heart.

While the invention is particularly directed to the art of noninvasive electrocardiographic imaging, and will thus be described with specific reference thereto, it will be appreciated that the invention may have usefulness in other fields and applications.

Cardiac electrical activity is a complex process that is both time dependent and spatially distributed throughout the myocardium. However, standard electrocardiographic techniques (i.e., ECG and vectorcardiography, VCG) are very limited in their ability to provide information on regional electrocardiac activity and to localize bioelectric events in the heart (in fact, VCG lumps all cardiac sources into a single dipole).

With recent advances in electronics and computers, simultaneous potential recordings from many (100 to 250) torso sites has become practical and inexpensive. The resulting body surface potential maps (BSPMs) over the entire torso surface have been shown to reflect regional electrical activity in the heart in a fashion that is not possible from conventional ECG techniques. However, BSPM techniques only provide a very low resolution, smoothed-out projection of cardiac electrical activity. Therefore, specific location of cardiac events (e.g., sites of initiation of activation or ectopic foci) and details of regional activity (e.g., number and location of activation fronts in the heart) cannot be determined merely from visual inspection of the BSPM.

In contrast, potential distributions over the epicardial surface of the heart accurately mirror details of the electrical events within the myocardium with high resolution. As a result, mapping of potentials directly from the epicardium has become an important experimental tool in the study of cardiac excitation and arrhythomogenesis. It has also become an essential clinical tool for diagnosis of arrhythmias, evaluation of treatment (e.g. antiarrhythmic drug therapy) and localization of cardiac electrical events (e.g. determining the location of the arrhythomogenic focus prior to ablation).

With the increasingly widespread use of nonpharmacological antiarrhythmic interventions (e.g. ablation), there is a growing need for fast and precise localization of electrocardiac events. It is highly desirable, therefore, to develop an imaging modality for the noninvasive reconstruction of epicardial potentials from BSPM data. Such an imaging modality could also be used, noninvasively, to identify patients at risk of arrhythmias and sudden death, and to evaluate the effects of intervention (e.g., drug therapy) in such patients.

The present invention provides a new and improved system and method for electrocardiographic imaging that overcomes the problems and difficulties of prior known systems.

SUMMARY OF THE INVENTION

An object of the present invention is to provide a system and method for noninvasively determining electrical activity on the surface of the heart of a human being wherein electrical potentials on the surface of the torso are monitored and body surface potential data, or maps, are then generated based on the electrical potentials determined. The geometry of the torso, locations of electrodes, the epicardial surface (or envelope) and position of the heart within the torso are then determined. A matrix of transformation is generated based on that data and regularized. An electrical potential distribution over the surface of the heart is then determined based on the regularized matrix of transformation and the body surface potential map. Electrograms and isochrones are also reconstructed on the epicardium.

In another aspect of the invention, the electrodes are disposed on a vest that is worn by the patient.

In another aspect of the invention, the geometry of the torso, the location of the electrodes, the epicardial surface (or envelope) and the position of the heart are determined by conducting a computed tomographic (CT) or magnetic resonance imaging (MRI) scan.

In another aspect of the invention, the geometry of the torso, the epicardial surface (or envelope) and the position of the heart are determined by conducting a biplane x-ray procedure.

In another aspect of the invention, determining the location of the electrodes and torso geometry includes implementing a digitizer.

In another aspect of the invention, determining the electrical potential distribution over the surface of the heart includes multiplying the regularized matrix of transformation by the body surface potential map.

In another aspect of the invention, epicardial electrograms are computed based on the electrical potential distribution.

In another aspect of the invention, isochrones are generated based on a derivative of the electrograms.

In another aspect of the invention, a system for implementing the above procedure is provided.

Further scope of the applicability of the present invention will become apparent from the detailed description provided below. It should be understood, however, that the detailed description and specific examples, while indicating preferred embodiments of the invention, are given by way of illustration only, since various changes and modifications within the spirit and scope of the invention will become apparent to those skilled in the art.

DESCRIPTION OF THE DRAWINGS

The present invention exists in the construction, arrangement, and combination of the various parts of the device and steps of the method, whereby the objects contemplated are attained as hereinafter more fully set forth, specifically pointed out in the claims, and illustrated in the accompanying drawings in which:

FIG. 14 shows measured and computed pacing sites on epicardial envelope meshes;

FIG. 15 shows measured torso potentials and measured and computed epicardial potentials;

FIG. 18 shows measured and computed isochrones;

FIG. 19 shows measured and computed isochrones;

FIG. 21 shows noninvasively reconstructed epicardial potentials and selected electrograms; and, FIG. 22 shows noninvasive reconstruction of epicardial potentials during normal sinus rhythm as well as a reconstructed electrogram.

DETAILED DESCRIPTION OF THE PREFERRED EMBODIMENTS

Figure 1:
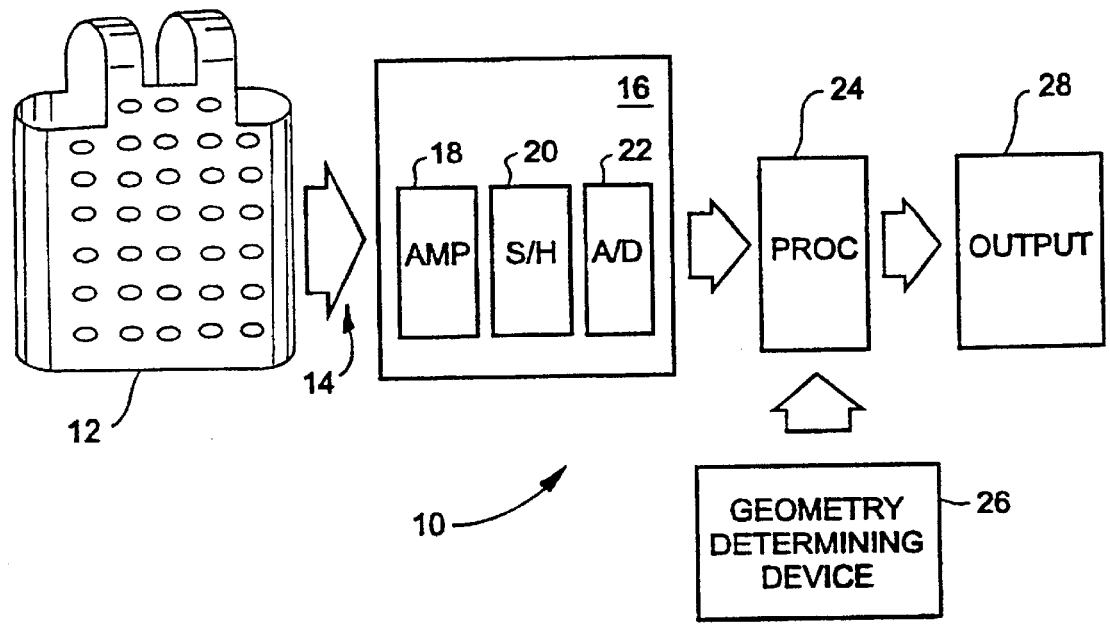
FIG. 1 is a functional block diagram illustrating the preferred embodiment of the present invention.

Referring now to the drawings wherein the showings are for purposes of illustrating the preferred embodiments of the invention only and not for purposes of limiting same, FIG. 1 provides a view of the overall preferred embodiment. As shown, the system 10 is comprised of an electrode vest 12 that is in communication via suitable connection 14 with circuitry 16. It should be recognized that the vest 12 has electrodes (unnumbered) disposed thereon and configured to cover as much of the torso as possible when in use. So, for example, although only front electrodes and the vest are shown, electrodes are preferably positioned on the back and sides of the vest as well. The vest itself may, of course, take various forms. The circuitry 16 includes amplifier circuitry 18, sample and hold circuitry 20 and analog to digital converter 22. The circuitry 16 supplies data to processor (or computer) 24 which also receives data from geometry determining device 26. The processor 24 processes the data received from the circuitry 16 and the device 26 and provides it to the output device 28. Of course, the output device 28 may be a printer or display device or any other output device that might be useful to analyze or view the data results obtained.

More specifically, this system 10 is an on-line and highly integrated 240 channel system, designed to be a stand-alone and portable unit with data acquisition and data processing capabilities. The vest 12 preferably includes 240 silver/silver chloride Ag/AgCl electrodes for acquiring ECG signals from the body surface, although experiments have shown that the number of electrodes could range from 120 to 250. The use of silver/silver chloride allows the electrodes to be used without gel. This is advantageous because use of gel with such a high concentration of electrodes might cause short circuiting. This dry-electrode vest design, i.e., no gel, also allows for rapid application of the electrodes to the patient. The vest additionally gives two-dimensional stability to the electrode array so that electrode spacing is maintained constant and electrode positions are easily determined (e.g. for generation of BSPMs or for inverse reconstruction of epicardial potentials). Further, the mapping system includes very high ($10^{12}$ ohm) input resistance amplifiers and driven shield electrode cables to maximize common mode rejection. Driven shield cables are coaxial and optically coupled to avoid shock to the patient. It is to be appreciated that other types of electrodes arrangements or ways to obtain body surface potentials might be used, although the vest 12 embodies the preferred form.

As to other elements of the preferred system, the amplifier circuit 18 is a low noise (<10 microvolts) and high stability ECG amplifier, a sample and hold circuit is provided for each amplifier to insure that all electrode signals are sampled at the same time (no time skew between electrode signals), and the A/D converter 22 is a 12-bit monolithic type with 5 microvolt resolution. Moreover, the preferred system features a flexible design in that it incorporates a variable gain (gains of 100, 200, 1000, 2000 are available), variable sampling rate (2000, 1000, 500, or 250 Hz), and variable band-pass filtering. This makes it a "universal" mapping system in the sense that (with a suitable electrode array) it could be used for body surface mapping, epicardial mapping, endocardial mapping or intracavitary mapping using a multielectrode probe. To insure patient safety, the digital and analog portions of the system are electrically isolated using optoisolators. Leakage current is limited to 10 uA under all conditions. The system design results in excellent signal quality (noise<10 microvolt rms., 72 dBS/N) so that a 4 microvolt level signal component in the ECG is accurately represented, without the use of electrode paste. All 240 channels are displayed at the time of data acquisition for inspection of quality.

Based on experimental torso-tank studies, as alluded to above, it has been determined that at least 120 body surface electrodes are necessary for inverse-computing of epicardial potentials with acceptable accuracy. The preferred mapping system meets this requirement and the dry-electrode/vest design makes patient studies with a large number of electrodes practical and fast.

Figures 2, 4:
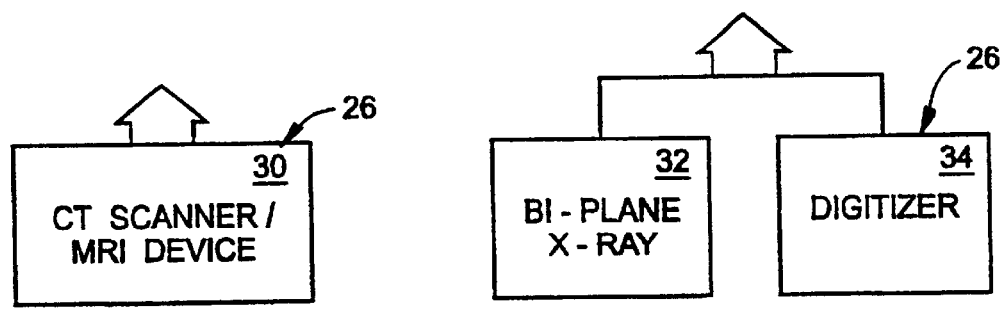
FIG. 2 is a functional block diagram illustrating exemplary geometry determining devices.
FIG. 4 is a functional block diagram illustrating another geometry determining device.
Figure 3:
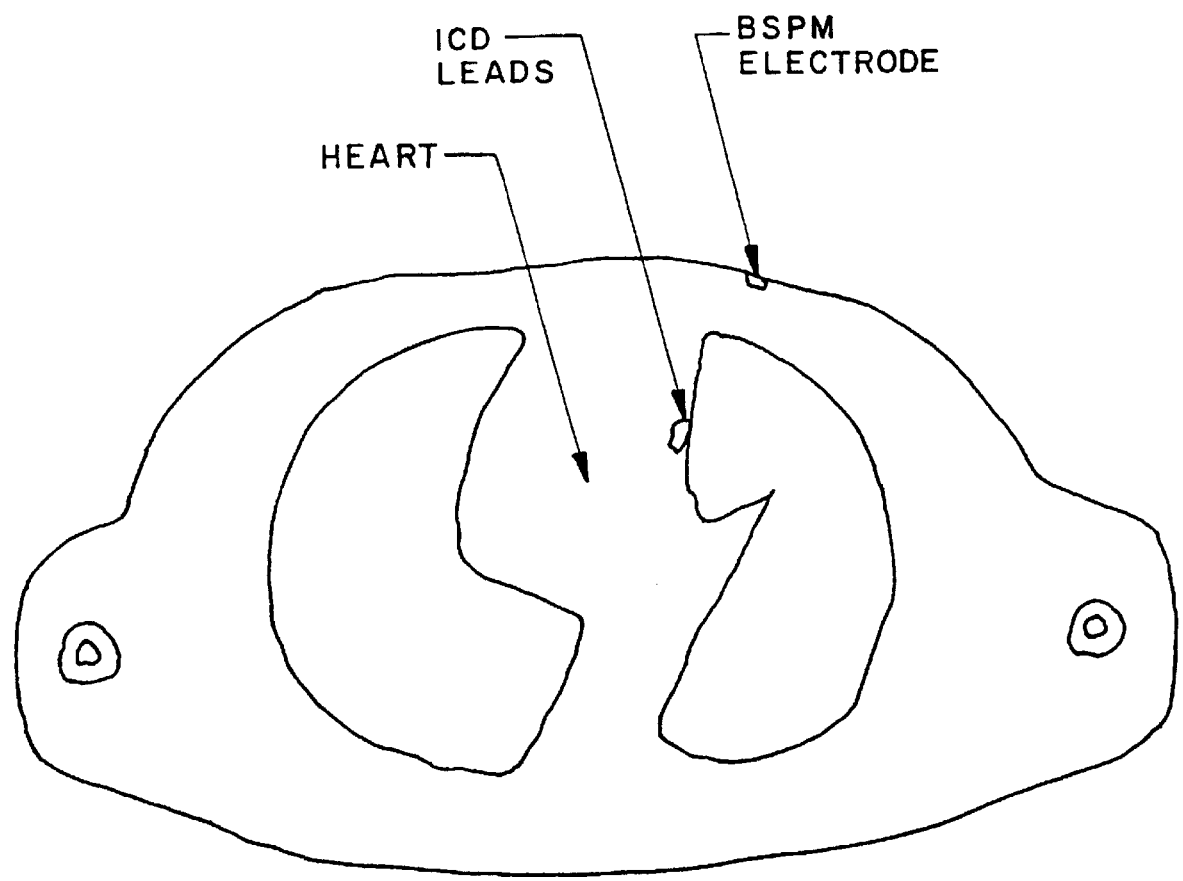
FIG. 3 is a reproduction of a CT scan used in connection with the present invention.

The geometry determining device 26 may take a variety of forms including x-ray, ultrasound, computed tomography (CT) and magnetic resonance imaging (MRI). For example, as shown in FIG. 2, the geometry determining device 26 may take the form of a CT scanner or MRI device 30. The operation and collection of data therefrom will be apparent to those of ordinary skill in the art. In this invention, the CT scanner/MRI device 30 is used to generate data, or images, to determine torso geometry and, consequently, body surface electrode positions as well as an epicardial envelope surrounding the heart. As those of skill in the art will appreciate, the epicardial envelope is a suitable estimate of the epicardial surface itself, which could also be determined. It should also be recognized that locating the epicardial envelope or surface necessarily involves location of the heart. Preferably, if a CT scanner is used, the scanner will allow slice thickness between 1 mm and 8 mm and have adjustable kVp and mAs settings to perform a variety of different types of CT scans of different parts of the body. Moreover, the acquisition times should be on the order of 3 seconds or less. FIG. 3 illustrates a CT scan obtained for use in connection with the present invention.

As a further example, as shown in FIG. 4, the geometry device 26 may take the form of a bi-plane x-ray machine 32 and a digitizer 34. This technique utilizes the three dimensional digitizer/locator 34 to obtain the torso geometry and the positions of body surface electrodes. The epicardial envelope is constructed from two bi-planar x-rays (30° right anterior oblique, and 60° left anterior oblique or other angles as required) using curve fitting techniques. Experiments have shown that two portable 3D digitizer systems (including two dedicated lap-top computers for data acquisition and storage) that are used together can digitize the entire torso in about 10 minutes. The preferred digitizers perform with 1 mm accuracy. Bi-planar x-rays are obtained with suitable x-ray equipment usually located in the catheterization laboratories.

Figure 5A:
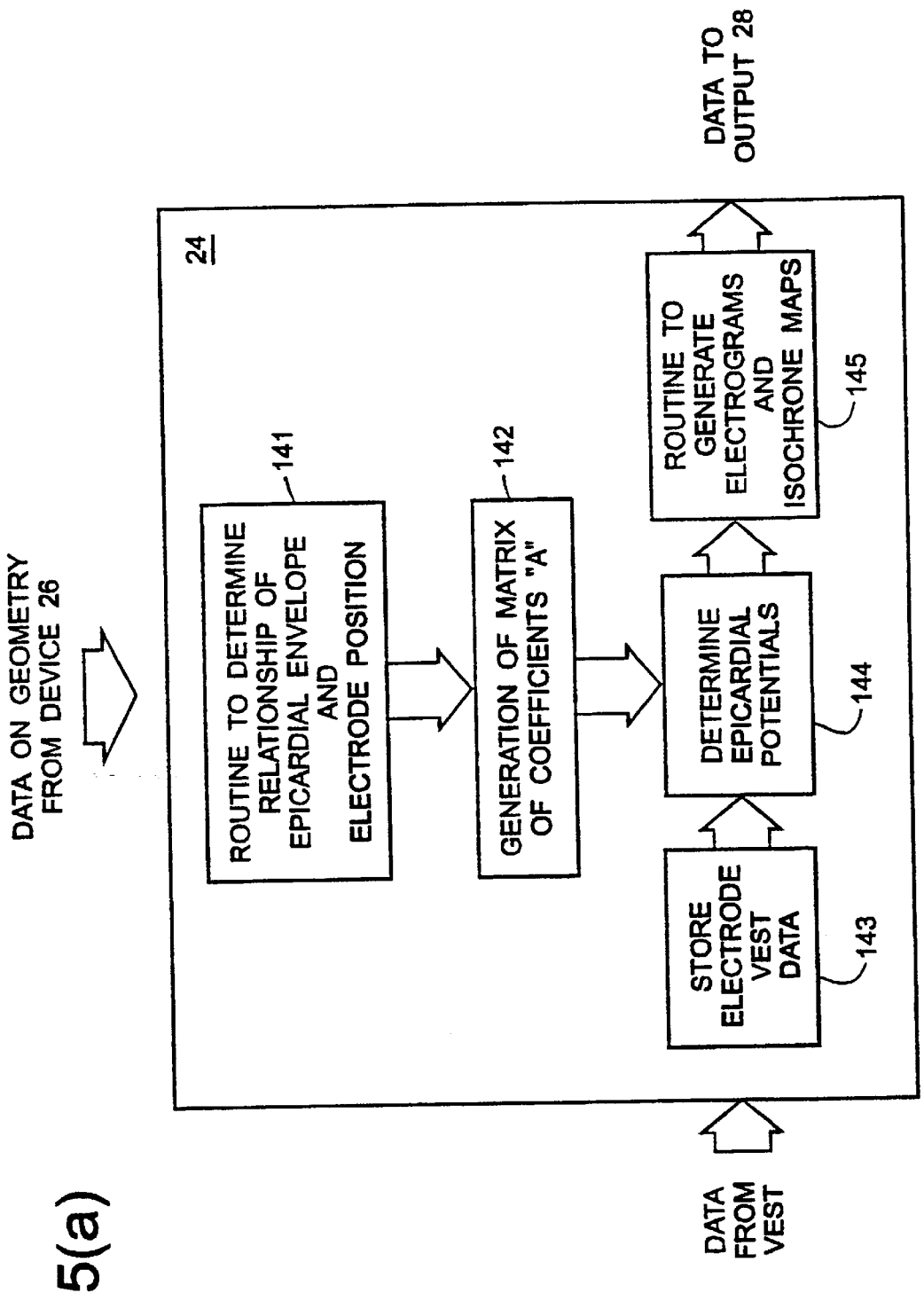
FIG. 5(a) is a functional block diagram of the processor according to the present invention.

Referring now to FIG. 5(a), functional blocks of the processor 24 are described. Those skilled in the art will appreciate that the processor 24 may actually include suitable software and hardware that accomplish the functions described. In one embodiment, a software tool implemented takes the general form of that described in connection with FIG. 5(b), although neither the processor nor the tool is so limited. For example, it should be recognized that the software tool of FIG. 5(b) has features involving testing and validation which are not specifically described in connection with FIG. 5(a) but modification to incorporate these features would be apparent to those of skill in the art.

Specifically, as shown in FIG. 5(a), data on geometry of the torso and vest (or electrode position) and the epicardial envelope (or surface) are input to the processor 24 from the device 26. Preferably, as noted above, the invention is implemented using bi-plane x-ray techniques with the noted digitizer or CT. These techniques result in determination of the geometric envelope that approximates the epicardium.

As is shown in FIG. 5(a), at least one of these known imaging techniques is available to provide data (or images) to determine a geometric relationship of the epicardial envelope surrounding the heart and electrode positions (or torso geometry) (block 141) based on the input of the device 26. A matrix of coefficients A, described in more detail below, is also generated (block 142) in the processor. In addition, data, i.e. electrical potentials measured on the surface of the torso, is input to the processor from the vest 12. These data are stored in the processor (block 143). Epicardial potentials may then be determined by the processor based on the stored electrical potentials and the matrix of coefficients (block 144). Electrograms and isochrone maps are also generated for display and evaluation (block 145). This information may, of course, be output.

Figure 5B:
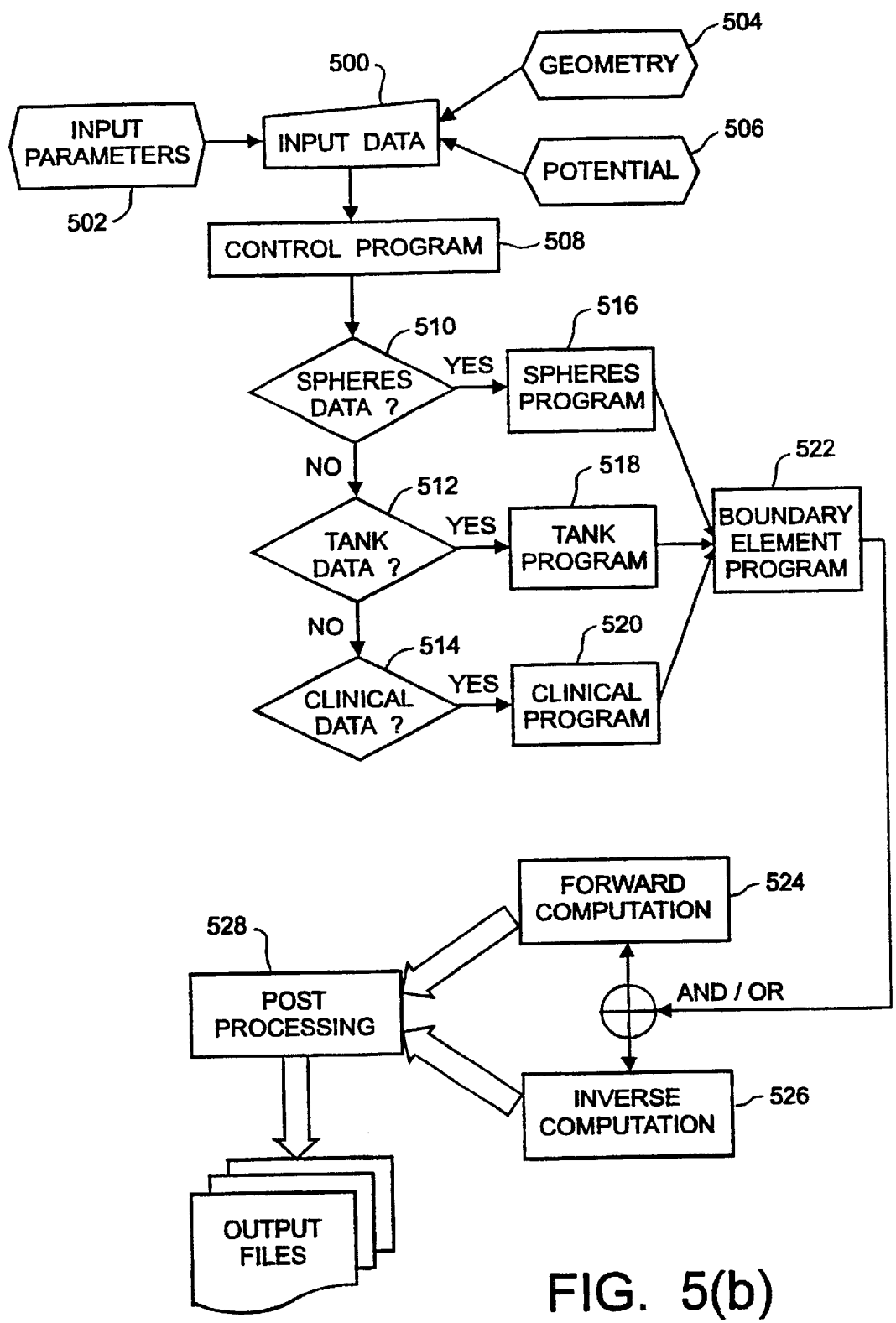
FIG. 5(b) is a flow diagram illustrating a software tool implemented according to the present invention.

As noted above, the software tool may take the general form of the flow diagram illustrated in FIG. 5(b), but those skilled in the art will appreciate that such a program, which (as will be described) also accommodates testing and validation processes, may well be modified and/or evolve into a modified tool (to resemble, for example, only the features described in connection with FIG. 5(a)) as the present invention is modified as a result of additional development or needs of users. Those skilled in the art will also appreciate that the description of this software tool necessarily overlaps with the description in connection with FIG. 5(a) because the processor of FIG. 5(a) implements such software tools in the described embodiment.

As shown, information is input to the system (step 500). Specifically, parameters are input to the system by the user (step 502). Geometry data and potential data are also input (steps 504, 506),. It should be recognized that in a clinical setting, the geometry data is generated by imaging device 26 and potential data is generated by electrode vest 12; however, if the software tool is implemented for testing and validation purposes, the geometry data may be known parameters, such as those associated with geometric spheres and torso tanks (used in testing), that are simply input to the system. The overall control program is implemented (step 508) and it is determined whether to use the software tool for testing and validation (using sphere or torso tank data (steps 510, 512) or clinical application (using clinical data) (step 514)). Appropriate processing is then conducted on the data (steps 516, 518 or 520), as will be apparent to those skilled in the art, to prepare the data for necessary mathematical manipulation.

Next, a boundary element method is applied (step 522). At that time, forward (step 524) or inverse (step 526) computations, as necessary, are performed. Of course, for clinical applications, only inverse computations (as described below) are used. Once the data is computed, processing of the data for output is accomplished (step 528).

Figure 6:
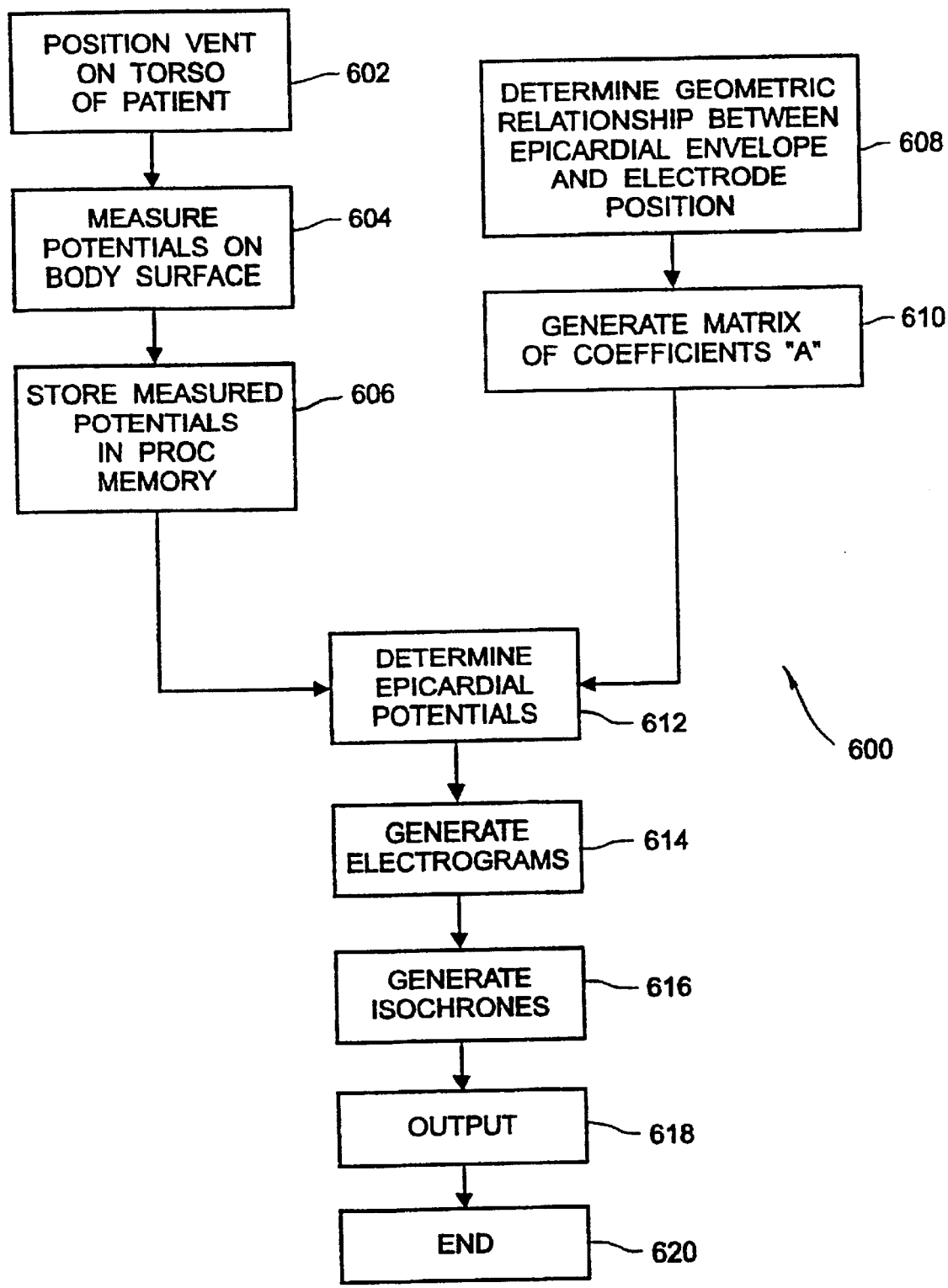
FIG. 6 is a flow chart showing the method according to the present invention.

Referring now to FIG. 6, the overall method 600 by which epicardial potentials may be determined according to the present invention is described. Initially, an electrode vest 12 is positioned on the torso of the human body (step 602). Potentials are then measured on the body surface (step 604) and stored (step 606).

A geometric relationship between the torso geometry, i.e. electrode positions of the vest in the preferred embodiment, and the epicardial envelope, or surface, is also determined (step 608). The geometry is, of course, determined using the geometry determining device 26. Based on this data on the geometric relationship, a matrix of coefficients A is generated (step 610).

Next, epicardial potentials are determined based on the stored potentials and the matrix of coefficients (step 612). Electrograms and isochrones are then generated by the processor (steps 614 and 616) and output (step 618). The procedure is then ended (step 620).

As will be appreciated by those skilled in the art upon a reading of the description of the present system and method, ECG imaging requires solving the inverse problem of electrocardiography. The mathematical computations accomplished by the processor 24 in doing so relate to and should be analyzed by considering "forward" computations, i.e. calculating torso potentials from known epicardial potentials, and "inverse" computations, i.e. calculating epicardial surface potentials based on measured torso potentials. Of course, the inverse computation is the computation that is used for implementation of the present invention (.e.g. step 612 in FIG. 6), but understanding the forward computation is also useful.

While various forward and inverse computations are known, the computations involved in connection with the present invention are as follows. More particularly, computation of torso potentials based on measured epicardial potentials (the "Forward Problem") requires solving Laplace's equation which entails the discretization of Laplace's equation (using Green's second theorem as described in, for example, Jackson J D, *Classical electrodynamics*, John Wiley and Sons, New York (1975)) in the volume between the epicardial surface and the body surface. A known boundary element method (BEM) (See, for example, Brebbia C A, Telles J C F, Wrobel L C, *Boundary element techniques. Theory and applications in engineering*, Springer Verlag, Berlin (1984) or Brebbia et al., *Boundary Elements: An Introductory Course*, McGraw-Hill, New York (1989)) is used to accomplish this task.

Below is a short description of the mathematical formulation. Details can be found in previous publications: Khoury D S, B. Taccardi, Lux R L, Ershler P R, Rudy Y, "Reconstruction of endocardial potentials and activation sequences from intracavitary probe measurements," *Circulation*, 91:845–863 (1995); Rudy Y, Messinger-Rapport B J, "The inverse problem in electrocardiography: solutions in terms of epicardial potentials," *CRC Crit Rev Biomed Eng.*, 16:215–268 (1988); Rudy Y, Oster H S, "The electrocardiographic inverse problem," *CRC Crit Rev Biomed Eng.*, 20:25–46 (1992); Messinger Rapport B J, Rudy Y. "Computational issues of importance to the inverse recovery of epicardial potentials in a realistic heart-torso geometry," [published erratum appears in *Math Biosci*, 99(1):141 (1990 April)], *Math Biosci*, 97:85–120 (1989); Oster H S, Rudy Y, "The use of temporal information in the regularization of the inverse problem of electrocardiography," *IEEE Trans Biomed Eng.*, 39:65–75 (1992); and, Messinger Rapport B J, Rudy Y, "Regularization of the inverse problem in electrocardiography. A model study," *Math Biosci*, 89:79–118 (1988), all of which are hereby incorporated herein by this reference.

The discretization noted above results in the following linear matrix relationship:

$$V_T = A V_E \quad (1)$$

where $V_E$ is the vector of epicardial potentials, $V_T$ is the vector of torso potentials and A is the $N_T \times N_E$ transfer matrix of influence coefficients between heart (or epicardial envelope) and torso (or electrode positions) that depends only on the geometry and the conductivities of the media in the volume. In the present preferred embodiment, the torso is treated as being homogeneous; however, the matrix A is also expandable to take into account torso inhomogeneities (e.g. lungs, etc.). Equation (1) represents the forward problem of electrocardiography, that is a computation of body surface potentials from potentials on the epicardium.

The matrix A in equation (1) is determined by the geometrical relationship between the epicardial surface or envelope and the torso. Specifically, it requires specification of node positions (corresponding to electrode positions) on the torso and node positions on the epicardium. Geometry data, as noted above, is obtained from the geometry determining device 26 which, again, may involve any of the known imaging modalities. Errors in determining the node positions on these two surfaces, may be amplified due to the nature of the inverse procedure and might consequently introduce errors in the reconstructed potentials. Accordingly, accurate determination of geometry is important for implementation.

The second aspect of the computational methodology is inverting equation (1) to obtain an expression for the epicardial potentials in terms of the body surface potentials. The ill-posed nature of the inverse problem in electrocardiography (i.e. its instability in the presence of noise) requires regularization of the solution. In this study, although other schemes could be used, a Tikhonov zero order regularization (See, Tikhonov A N, Arsenin V Y, "Solutions of ill-posed problems," (trans from Russian) Wiley, N.Y. (1977), or Tikhonov et al., "Solutions of ill posed problems," 27–94, VH Winston & Sons, Washington D.C. (1977) which are hereby incorporated herein by reference) is used to stabilize the solution. This entails finding the epicardial solution, $V_E$, that minimizes the following objective function:

$$\min_{V_E}[\|AV_E - V_T\|^2 + t\|V_E\|^2] \quad (2)$$

or, more generally, minimizes $$\|V_T - AV_e\|^2 + tF[V_e]$$

The first term in equation (2) represents the least-square solution of equation (1). The second term in equation (2) is a regularization term that imposes bounds on the amplitude of the solution. The regularization parameter, t, controls the degree of the imposed constraint. It provides a balance between the accuracy and stability of the solution, resulting in a close estimate of the epicardial potential distribution that is also stable. In this work the regularization parameter, t, is found using the CRESO (Composite Residual and Smoothing Operator) method. (See, for example, Colli Franzone P, Guerri L, Tentoni S, Viganotti C, Baruffi S, Spaggiari S, Taccardi B, "Mathematical procedure for solving the inverse problem of electrocardiography," *Math Biosci*, 77:353–96 (1985), and Colli-Franzone et al., "Finite element approximation of regularized solutions of the inverse problem of electrocardiography and applications to experimental data" Calcolo, 1985, 22:91–186, which are incorporated herein by reference) and has been found to perform comparably to the "optimal" t that provides the minimum RMS error between the computed $V_E$ and the measured $V_E$. See, Messinger Rapport B J, Rudy Y, "Computational issues of importance to the inverse recovery of epicardial potentials in a realistic heart-torso geometry" [published erratum appears in Match Biosci 1990 April;99(1):141], *Math Biosci*, 97:85–120 (1989), which is incorporated herein by reference. The CRESO t depends only on the vector $V_T$ and the matrix A. Computing the epicardial potentials $V_E$, therefore, is completely noninvasive, requiring only the knowledge of the geometry (for the matrix A) and the torso electric potentials $V_T$.

Figure 7:
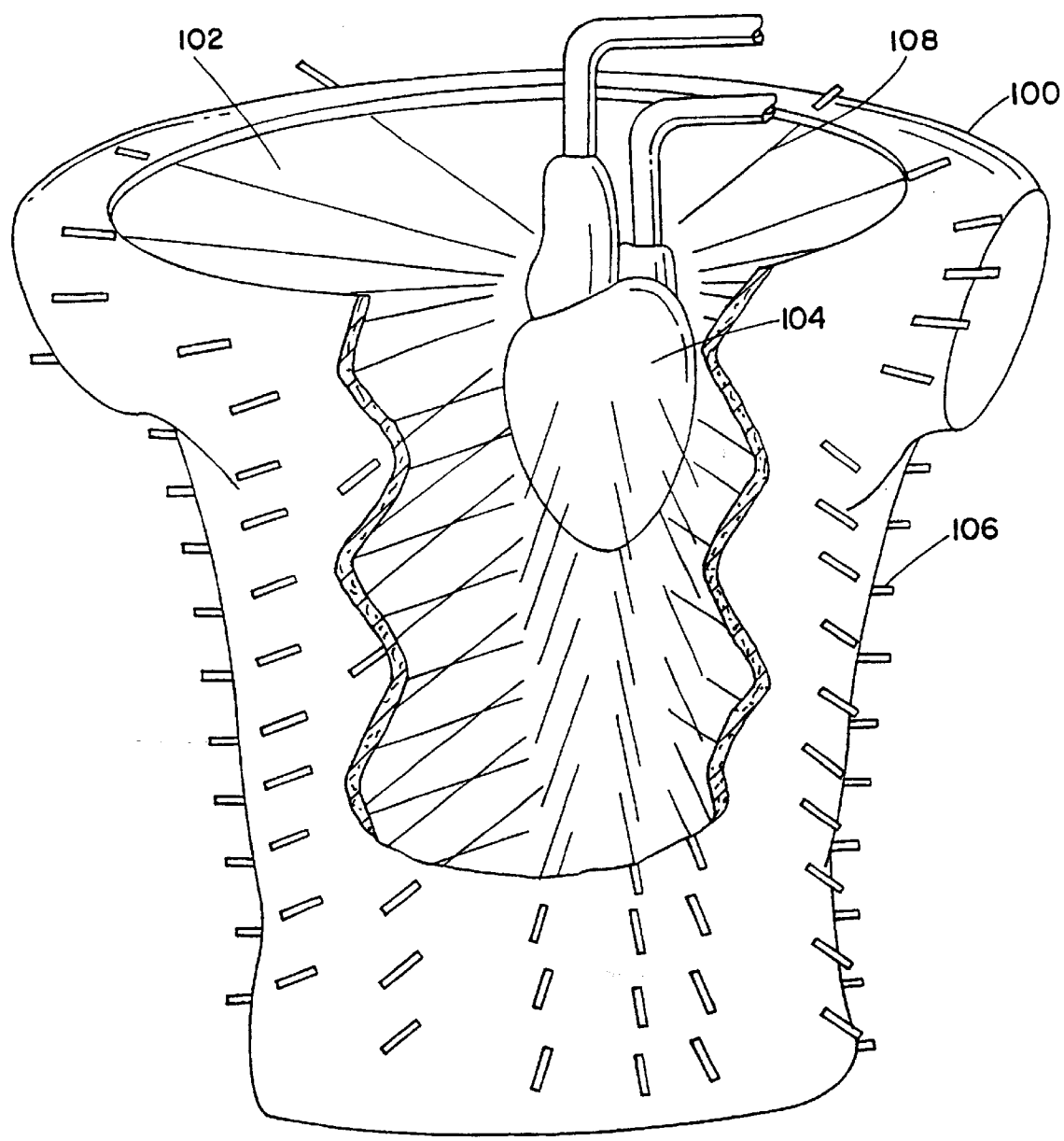
FIG. 7 illustrates an experimental torso-tank arrangement.

The inverse epicardial solutions were verified using a human shaped torso-tank (FIG. 7). The tank 100, molded from the torso of a 10 year old boy, was filled with an electrolytic solution 102 and contained an isolated dog heart 104 suspended in the proper human anatomical position. A second dog served to provide circulatory support for the isolated heart, using a modified Langendorff preparation which is stable for at least 4–5 hours. The tank's electrode system for measuring electric potentials (FIG. 7) consisted of 16 rows, each of 24 electrodes (exemplary shown at 106) equally spaced on the body surface in the polar angle, θ. In addition to the 384 body surface electrodes, there were 918 electrodes along 384 rods (exemplary shown at 108) that projected from the body surface into the volume toward the heart. All rods in the lower six rows were fixed; the rods in the upper ten rows were fixed only in the cylindrical coordinates z (defining a given horizontal cross section) and θ (the polar angle). They were free to move in the radial direction, and were pushed inward toward the heart once it was suspended in the tank (see FIG. 7). The rod tips were approximately 1 cm from the surface of the epicardium. Potentials were also measured on a 64-electrode sock (not shown) in direct contact with the epicardium.

Figure 8:
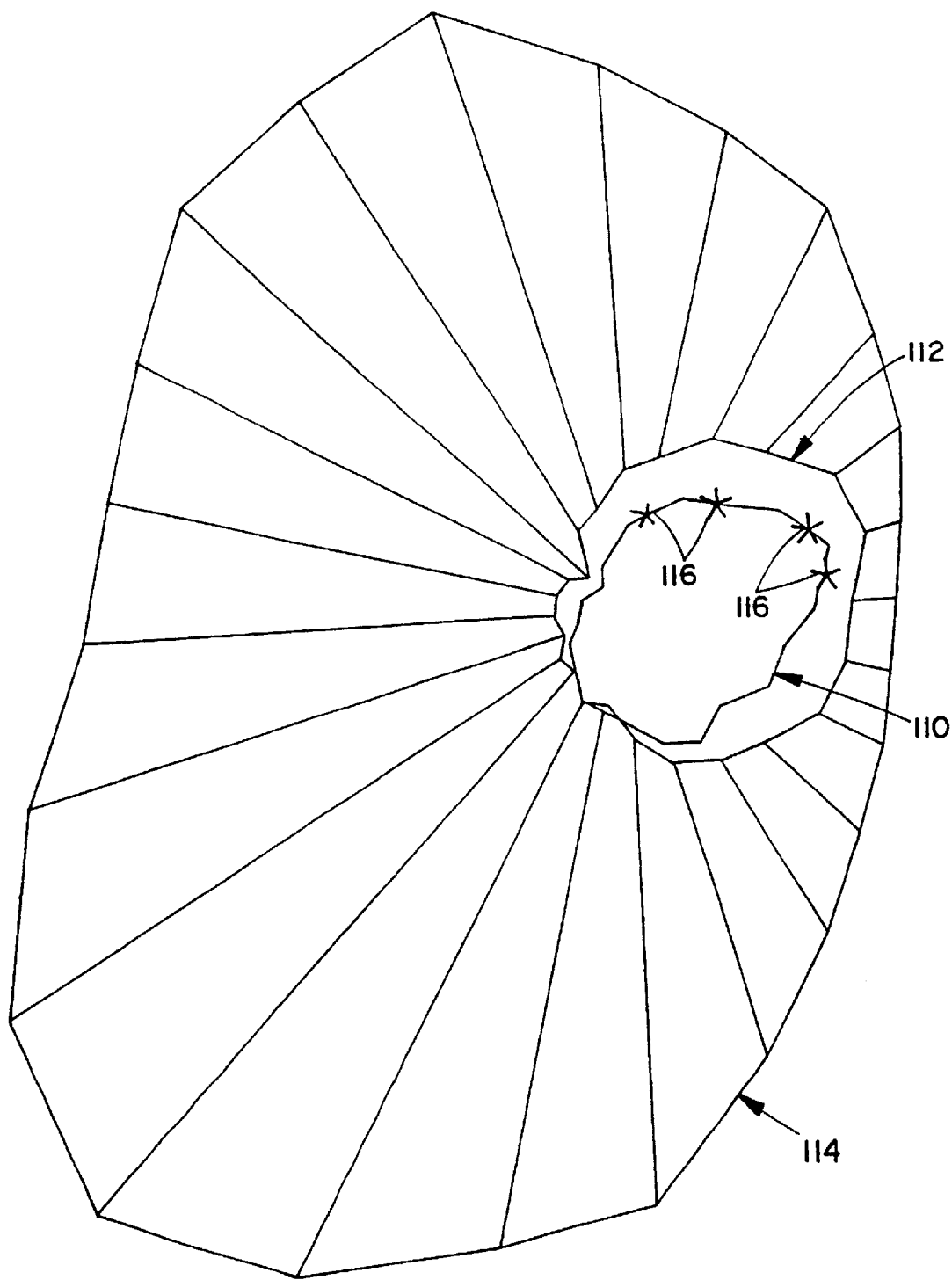
FIG. 8 is a cross section of the tank of FIG. 7.

FIG. 8 shows the rod-electrode configuration for one cross section of the tank. The inner-most contour 110 depicts the approximate heart boundary at this level. The next contour 112 connects the rod-tip electrodes ("epicardial envelope"), and the outermost contour 114 represents the body surface. The four asterisks 116 on the inner contour depict the positions of the four pacing sites (see below).

Figure 9:
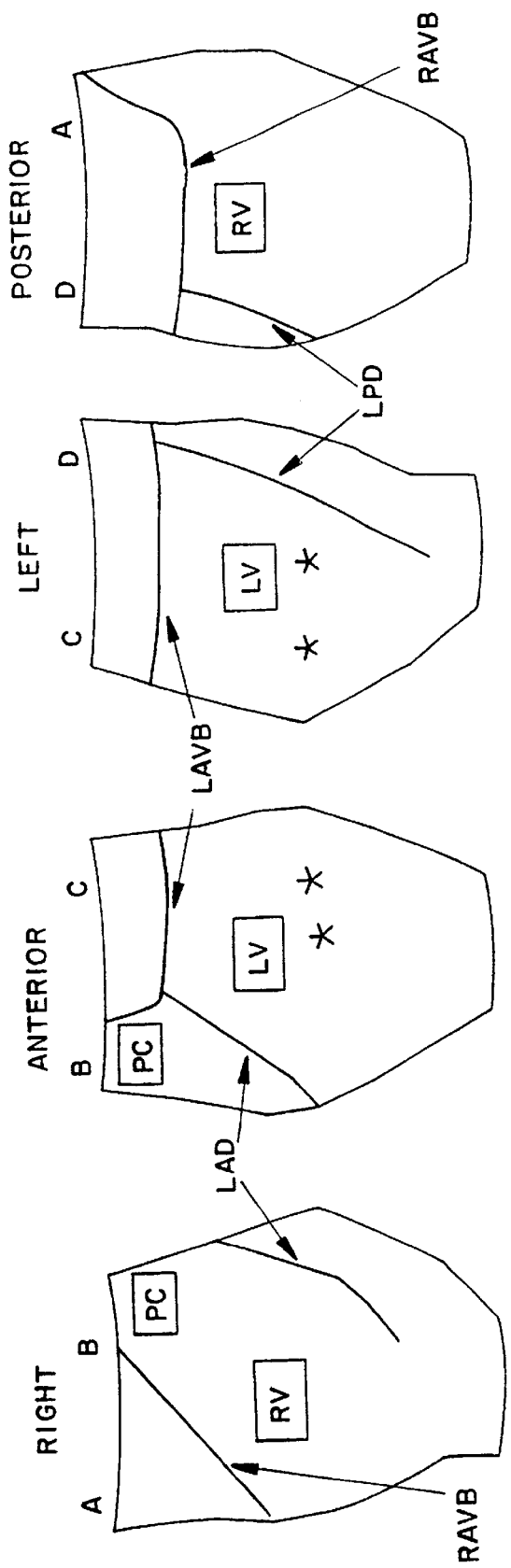
FIG. 9 illustrates a display format for an epicardial envelope surface.

FIG. 9 displays four overlapping views of the epicardium. Anatomical landmarks are displayed and identified beneath the plot. The symbols (clubs, hearts, diamonds, spades) identify overlapping regions in adjacent views in this figure as well as others. In addition, the four asterisks identify the pacing sites that are also displayed on the inner contour of FIG. 8.

For the purposes of this work, the electric potentials measured on the torso provided the input to the inverse procedure, and the potentials measured at the rod tips, which constituted an effective envelope around the heart, provided the experimental verification of the inverse solution. The epicardial envelope was used instead of the epicardial sock since it provided more controlled conditions for evaluating the reconstruction procedure. The geometric positions of the rod-tip electrodes comprising the epicardial envelope were measured directly and in the same frame of reference as the torso electrodes. In contrast, the positions of the sock electrodes were only known relative to each other and in their own reference frame. Because of this inaccuracy, the epicardial envelope provided a more controlled environment in which to study and test the inverse methodology without additional uncertainty caused by geometric error. A potential disadvantage of using the epicardial envelope is the possible degradation of the potential patterns due to their distance from the epicardium. It was found (not shown here) that, in general, the potential patterns are not degraded—only potential amplitudes may be somewhat lower on the envelope as compared to the sock. The data were acquired using a multiplexing system; 1336 electrodes divided among 8 banks (192 leads at a time). The data banks were time-aligned using 5 leads common to all banks. The signals were unipolar with reference to Wilson's central terminal. Other characteristics: sampling rate of 1 kHz (with sample and hold circuits), 12-bit resolution, and on-line amplification. All signals were gain-adjusted using calibration signals, and the baseline was subtracted.

Pacing was performed using subepicardial electrode pairs on four needles in the left ventricle and an additional electrode pair on the right atrium near the sinoatrial node. The four ventricular pacing sites were located along an imaginary line parallel to the atrio-ventricular (AV) groove and approximately halfway between it and the apex. Site #1 was located near the septum (see FIG. 8 for a cross-sectional view and FIG. 9 and for a surface view), sites #2, #3, #4 were at locations to the anatomical left of site #1, such that site #4 was located on the posterolateral left ventricle. Intersite distances between sites #1 and #2, between #2 and #3, and between #3 and #4 were approximately 15 mm, 20 mm and 17 mm respectively. Each site was paced individually. Simultaneous dual pacing of sites #1 and #4, sites #1 and #3, and sites #3 and #4 tested the resolution of the inverse solution at intersite distances of approximately 52 mm, 35 mm and 17 mm respectively. Because of the eccentric location of the heart within the torso, the various epicardial pacing sites were located at varying distances from the chest wall. Measured along a line perpendicular to the epicardium, the distances from each of the four sites (#1 to #4) to the chest wall were approximately 19 mm, 26 mm, 82 mm, and 99 mm, respectively. Ventricular pacing was accomplished with current pulses of 2 ms duration, and intensity just above threshold (generally 0.2–0.5 mA). Stimuli were delivered simultaneously to the ventricular pacing leads and to the right atrial pacing leads to prevent sinus beats from capturing the ventricles. Cycle length of pacing was approximately 380 ms.

Figure 10:
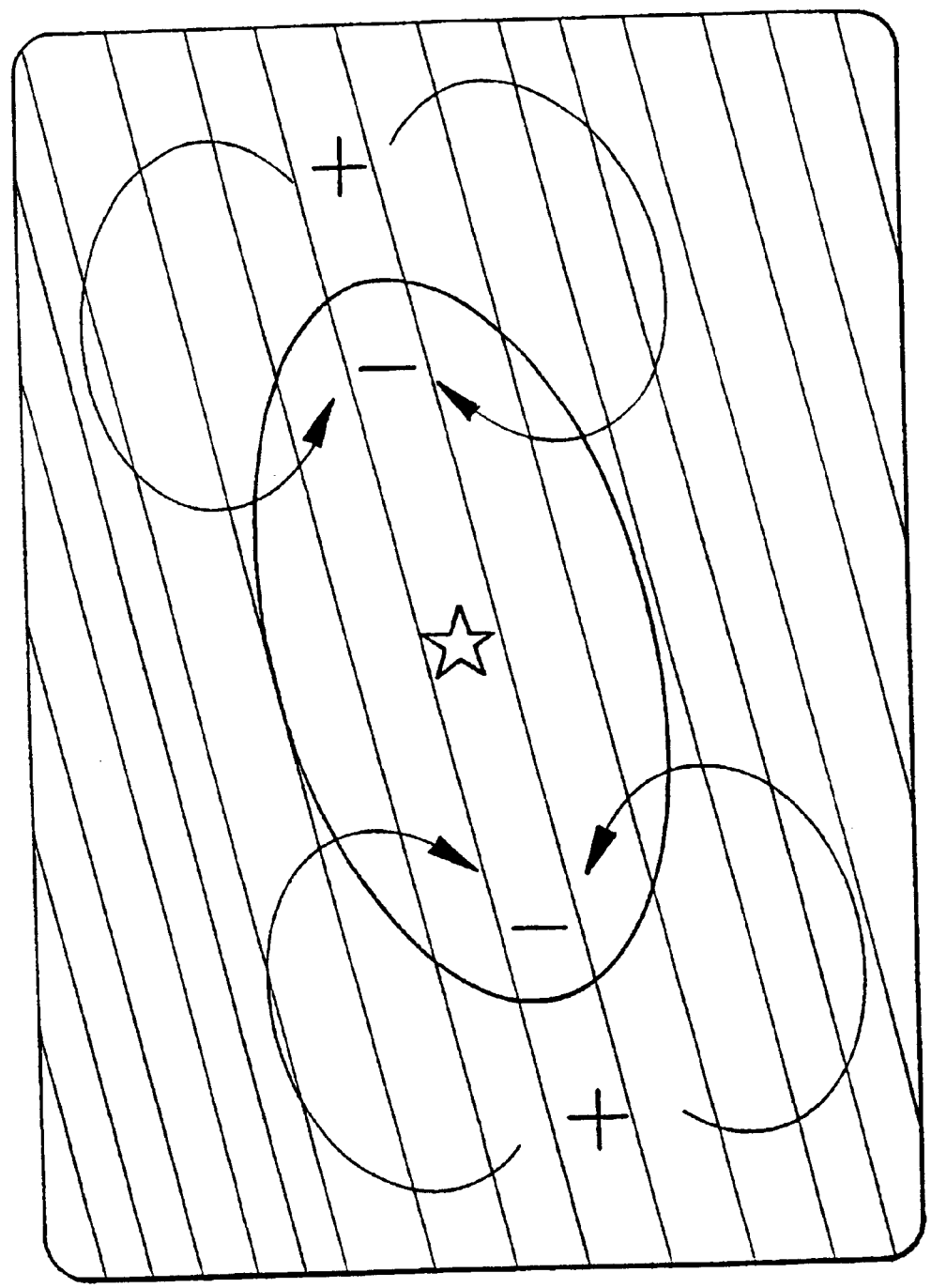
FIG. 10 is an illustration of potentials and currents associated with epicardial pacing.

FIG. 10, modified from Taccardi B, Macchi E, Lux R L, Ershler P R, Spaggiari, Baruffi S, Vyhmeister Y, "Effect of myocardial fiber direction on epicardial potentials," *Circulation*, 90:3076–90 (1994), is a schematic of the basic epicardial patterns of potentials and currents (arrows) associated with epicardial pacing. With epicardial pacing (central asterisk) a region of negativity forms (inside the ellipse in the figure). Because of the preferential activation along the fibers (shown as gray lines in the background), maxima (plus signs) form outside this negative region along the axis of the fibers. Notice that two corresponding minima (minus signs) form inside the negative region, and that neither minimum coincides with the pacing site. This potential pattern is consistent with an equivalent source configuration of two opposite axial dipoles pointing from each minimum towards its corresponding maximum. Based on these properties, the pacing site is determined to be at the center of the region of negativity in both the measured and the inverse-computed maps. If we detect only one minimum in the region of negativity it is because the epicardial potentials are determined with insufficient resolution to separate both minima. In such cases, the center of the elliptical negative region is still used to identify the site of pacing. Ideally, the negative region is quasi-elliptical in shape. In the experiments, this region approximates an ellipse, particularly during the early stages of propagation. Its center is determined as the intersecting point of the major and minor axes of an ellipse that best fits the negative region.

The torso potential data are displayed as contour maps in two views (anterior and posterior). The epicardial potential and isochrone data are shown as contour maps in four overlapping views (see FIG. 9). A stylized epicardium, very close in shape to the real epicardial rod-tip envelope, was created for this display so that the epicardial potentials could be presented on a smooth surface. This prevented misinterpretation of the potential maps caused by small surface discontinuities when the real, non-smooth epicardial (rod-tip) surface was projected onto two dimensions.

Isochrones for both measured and reconstructed epicardial data are computed by taking the time of epicardial activation at a given location as the time of maximum negative dV/dt of the temporal electrogram ("intrinsic deflection") at that location. For the computed epicardial maps, first a potential map for each time frame is computed in a quasi-static fashion for every millisecond throughout the activation process, then the time series of maps is organized by lead to provide temporal electrograms, and finally, the intrinsic deflection for each lead is determined. In some cases, it is clear that the automated procedure for computing isochrones chooses the incorrect time of activation. This can happen when the activation time is found in a region of high frequency noise, or where there are discontinuities in the electrogram caused by the quasi-static inverse reconstruction of discrete maps in time. In these situations the time of activation is corrected manually by taking information from the neighboring electrograms into account. Note that these isochrones are constructed on the epicardial envelope defined by the rod-tip electrodes and not directly on the epicardium. In this sense they constitute "pseudo-isochrones" on a surface close the epicardium but not on the epicardium itself.

Figure 11:
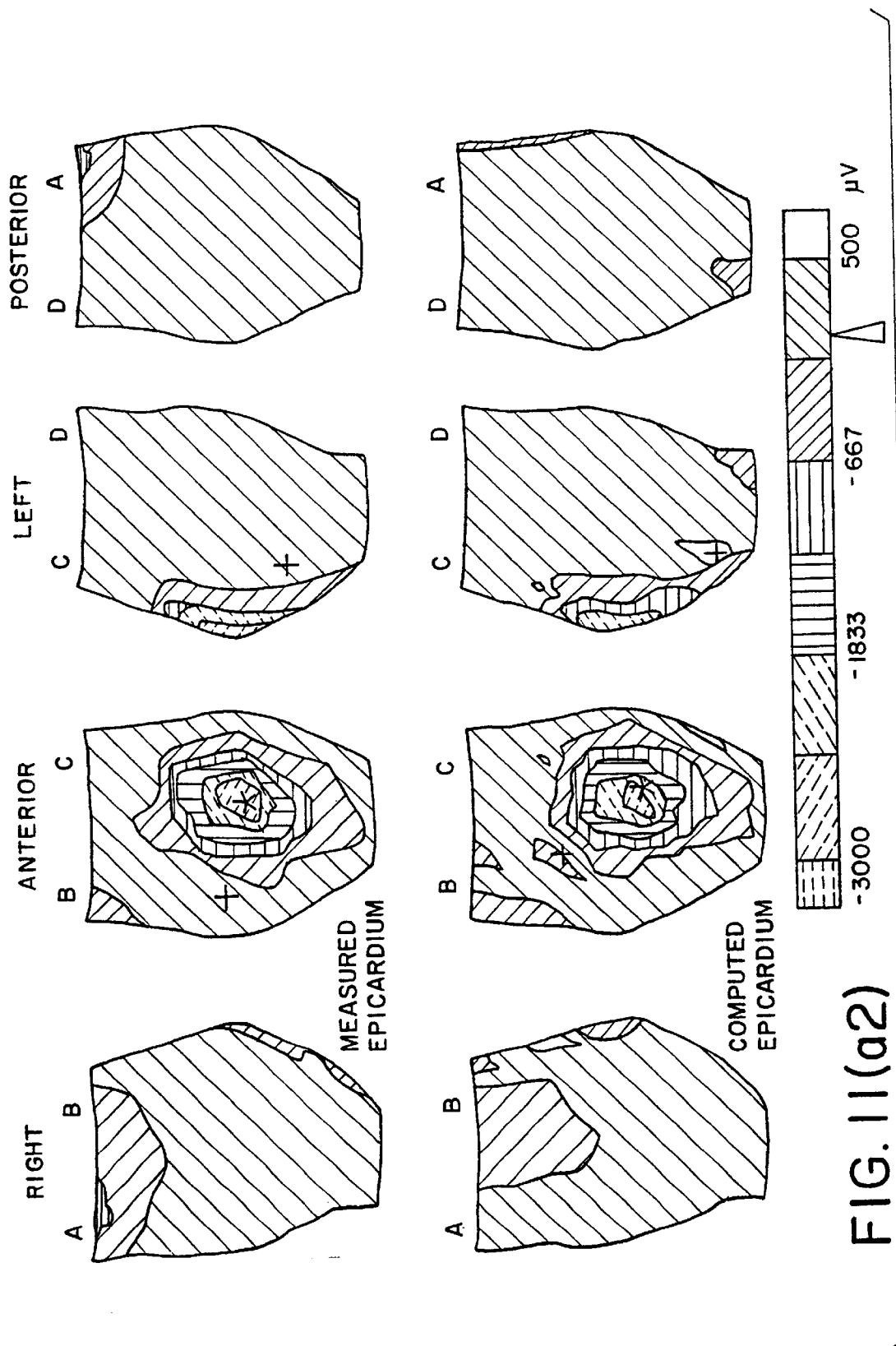
FIG. 11 shows measured torso potentials and various measured and computed epicardial potentials.
Figure 11:
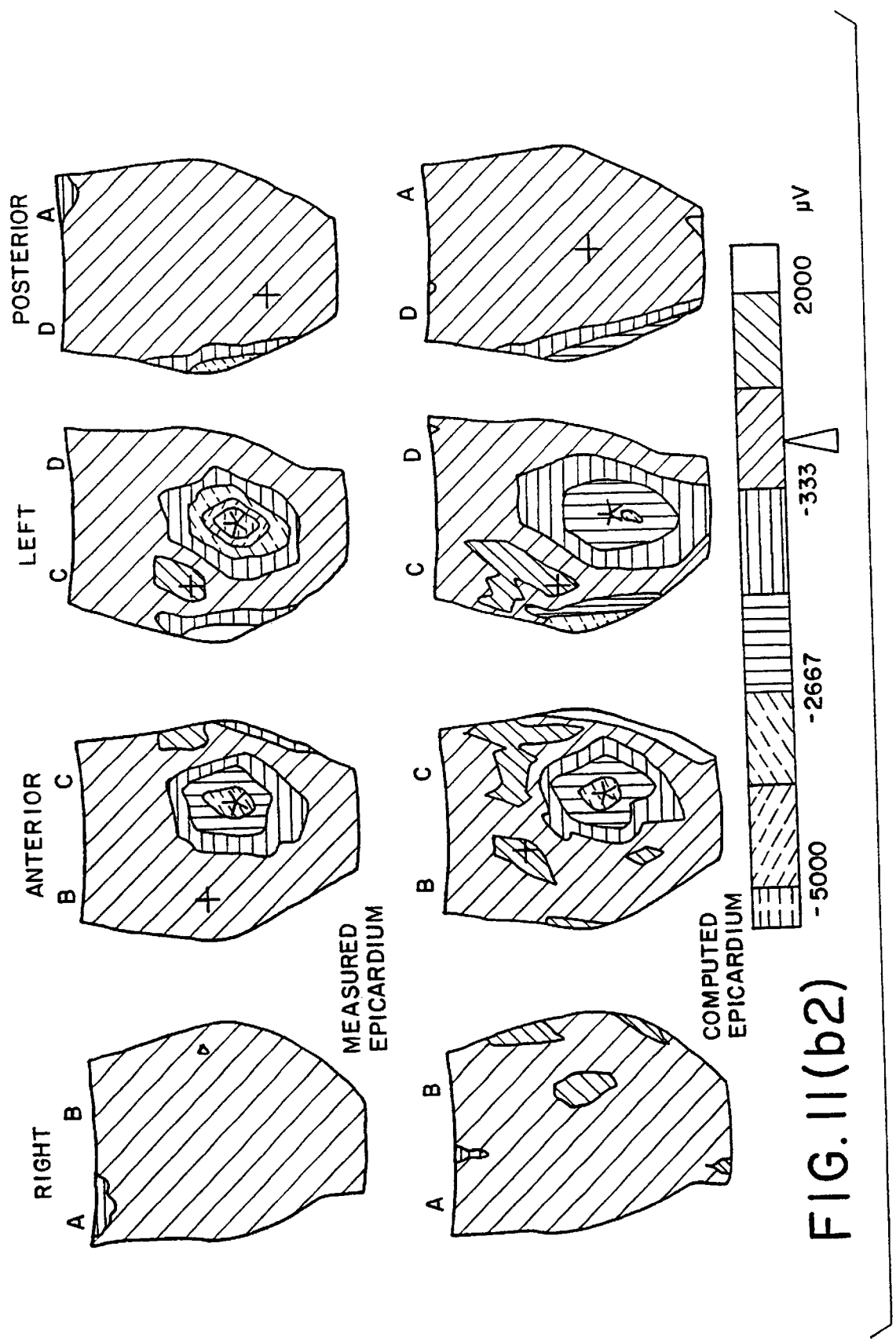
Figure 11:
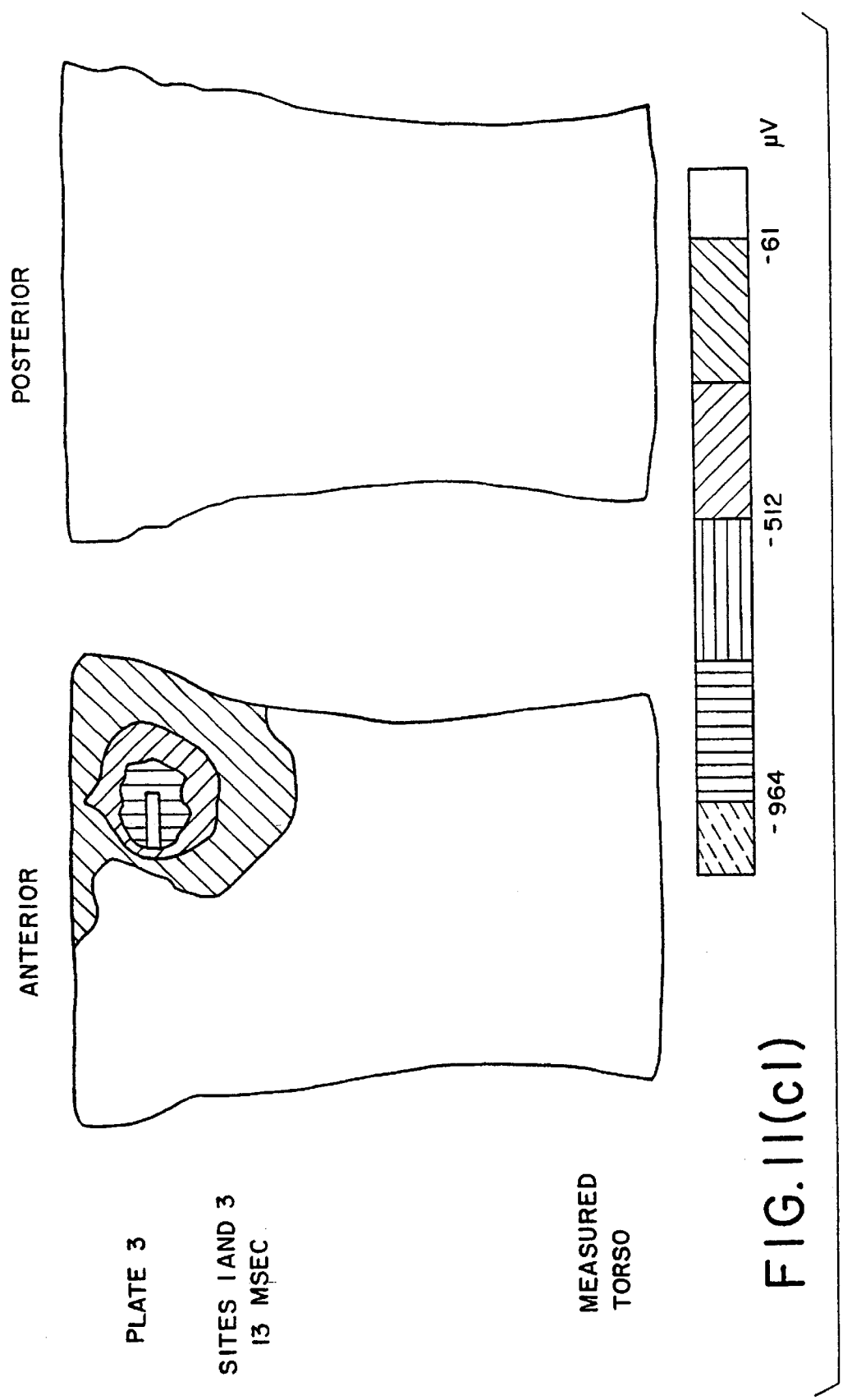
Figure 11:
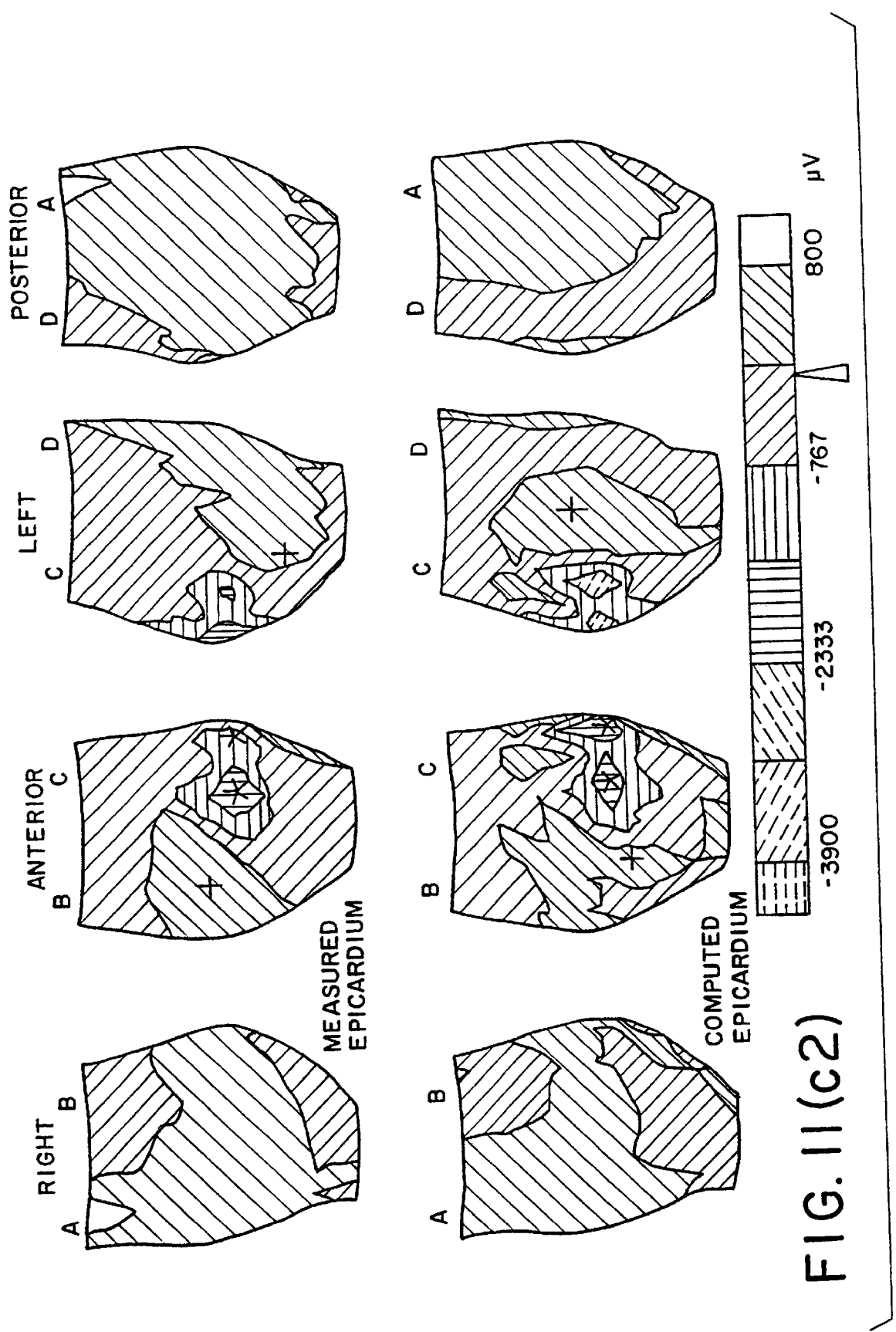

Examples of Non-Invasive Reverse Reconstruction
Single Pacing Sites:

As shown in FIG. 11, Color Plate 1 (top plate) shows the electric potentials for the first epicardial pacing site (site #1, see methods), and its format is similar to that of the subsequent color plates 2 and 3. Measured torso potentials (anterior and posterior views) are displayed on the left. The top and bottom rows on the right portion of the plate show the measured and inverse-reconstructed epicardial potential distributions, respectively. Each is displayed with the four overlapping views of FIG. 9. All potentials are displayed as color contour plots; see caption for format details.

In this color plate, the first (#1, most anterior) pacing site is stimulated, and an intense minimum (dark blue) is seen on the anterior view of the measured epicardial potentials (top row on the right of the plate). In the torso potential distribution, there is also a single minimum anteriorly, demonstrating that the epicardial potentials are reflected on the body surface. Using the torso potentials to reconstruct the epicardial potentials noninvasively (bottom row on the right of the plate), the intense minimum is reconstructed. In addition, the maxima flanking the minimum are seen in both the measured and the computed epicardial plots. The pacing site is marked with the asterisk. The reconstructed pacing site is located approximately 7 mm from its measured location. The two maxima are reconstructed 20 and 28 mm, respectively, from their measured locations.

Figure 12A:
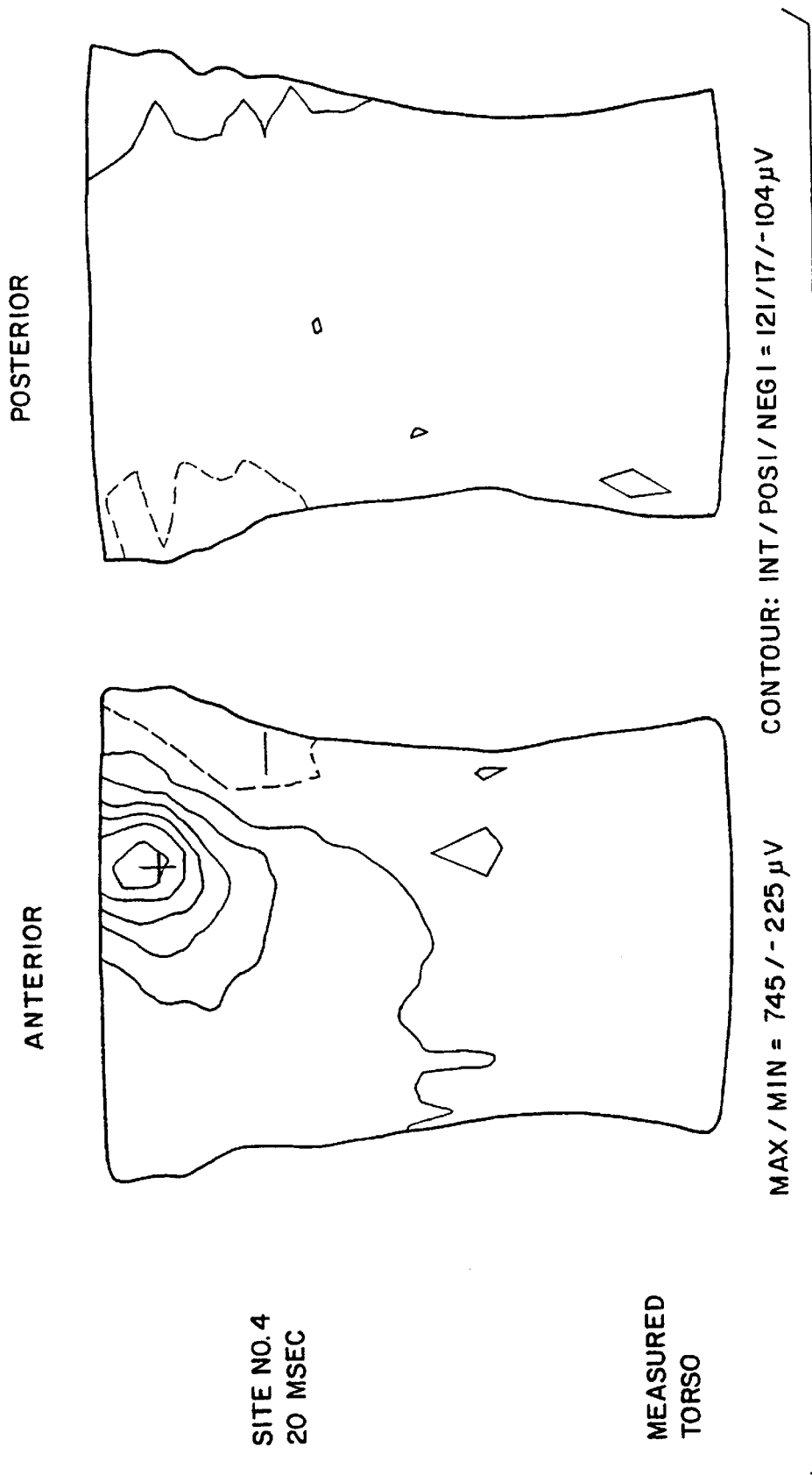
FIG. 12 shows measured torso potentials and measured and computed epicardial potentials.
Figure 12B:
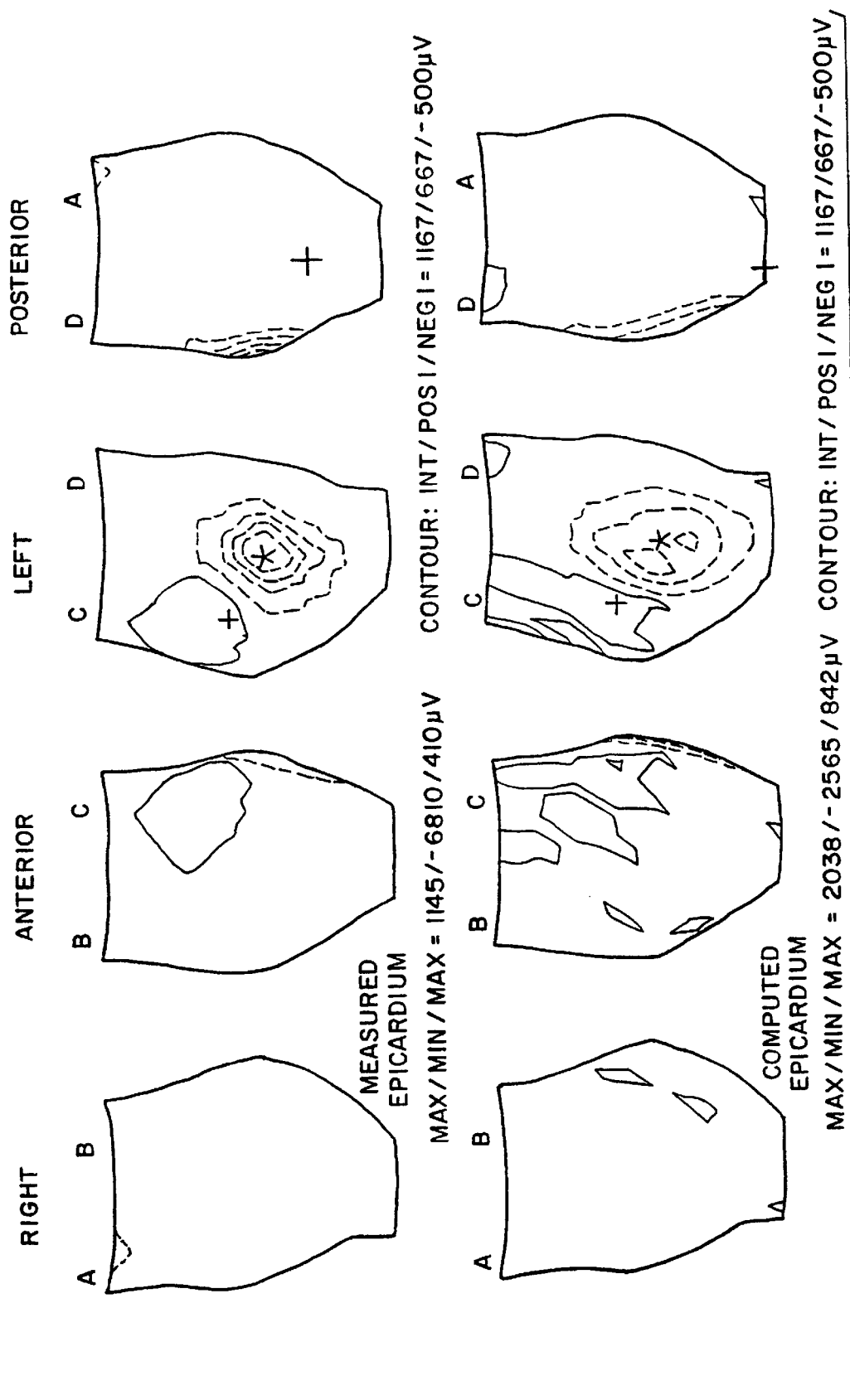

In FIG. 12, the most posterolateral pacing site (#4) is shown. The format for this and subsequent black-and white contour plots includes positive contours shown in solid lines, negative contours shown in dashed lines, maxima shown by +, pacing sites shown by *, minima shown by -, and magnitudes of identified extrema are shown below each plot in order of appearance. Contour interval, first positive, and first negative are also shown.

In FIG. 12 (as in plate 1, top), there is also one minimum seen on the torso. This minimum, however, is shifted more posteriorly as compared with that of plate 1; the anterior maximum is more prominent here. In the measured epicardial potentials, one sees a single minimum and an asterisk in the center of an elliptical negative area which reflects the pacing site, with two flanking maxima. In the noninvasively computed epicardial potentials the negative area contains two minima. These dual minima constitute the expected potential pattern as described in the discussion of FIG. 10. In our experiments these minima are rarely detected since the resolution (electrode density) is not sufficient. It is interesting that the minima are noninvasively reconstructed in their expected positions in the computed map despite their not being detected in the measured map. This can be explained by the fact that while the measured data are obtained with only 4 or 5 electrodes over the entire region of negativity, the computed potentials use data from the entire body surface. It is conceivable, then, that the computed potentials may have a better resolution than the measured potentials. The reconstructed pacing site (center of the ellipse, asterisk) is approximately 4 mm from the position of the measured site. The position of the reconstructed maxima are 0 mm and 28 mm from their respective measured locations. The error is reported as location errors of the noninvasively reconstructed maxima, minima and pacing sites (relative to the measured ones) on the effective epicardial surface (composed of rod tip electrodes). Because in the regions of these pacing sites the nodes (rod-tip electrodes) are spaced on the order of 15 mm apart, if the reconstructed extremum is shifted by only one electrode position, it will have an error of approximately 15 mm; two electrode positions, approximately 30 mm. Note that this error, reported on the effective epicardial surface, is larger than it would be on the epicardium itself because the effective epicardial surface is approximately 1 cm outside of the epicardium, and distances on this surface are greater than their projections on the actual epicardium. For example, the rod-tip electrodes that measure the minima of pacing sites #3 and #4 are located approximately 26 mm apart, but when the same rods are pushed in so that the rod tips touch the epicardium, these same rod-tip electrodes are approximately 17 mm apart. One must, therefore, bear in mind that the actual epicardial error may be less than the reported error on the epicardial envelope.

Figure 13:
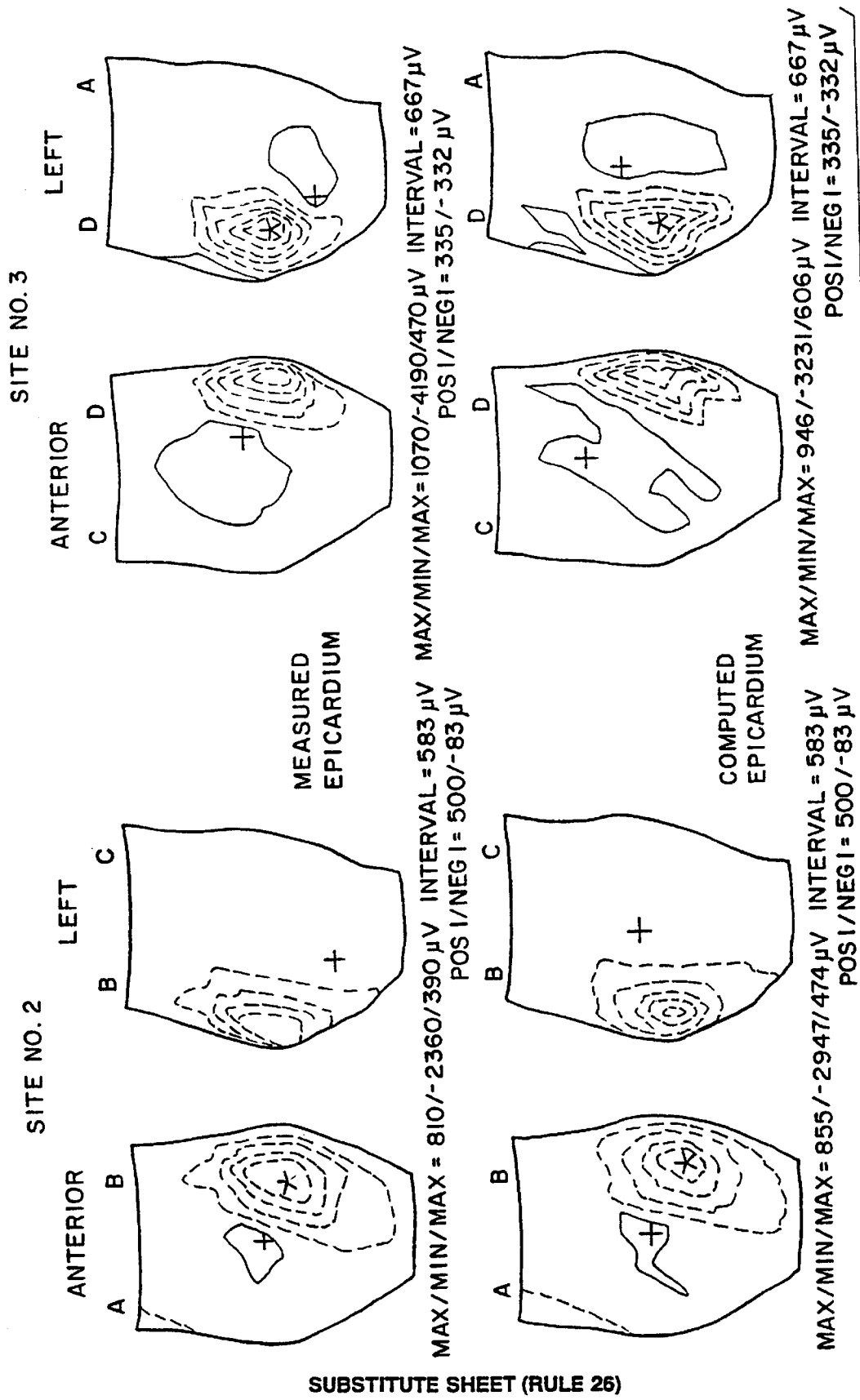
FIG. 13 shows measured and computed epicardial potentials.
Figure 16A:
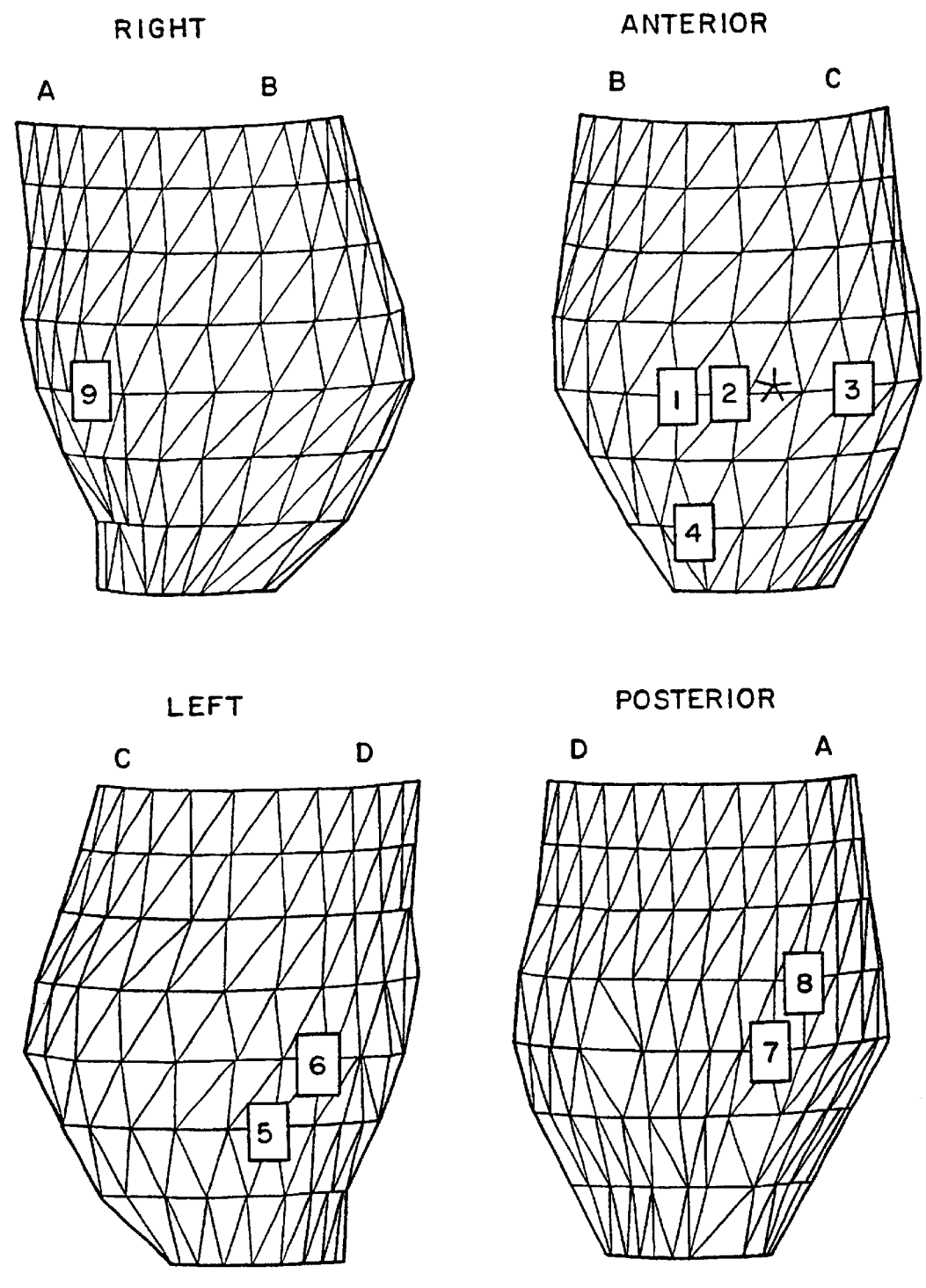
FIG. 16 shows epicardial envelope surfaces as well as measured and computed electrograms.
Figure 16B:
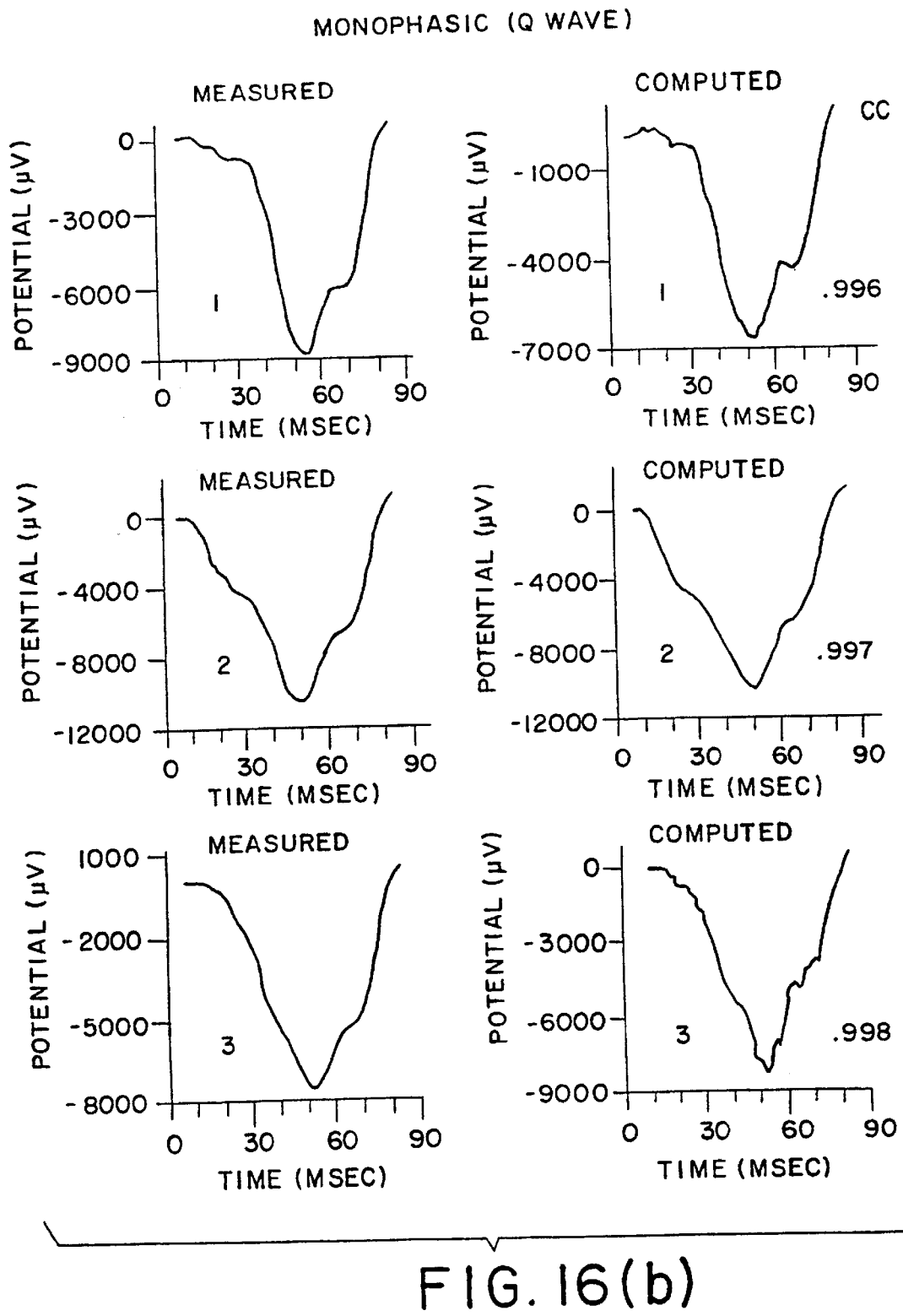
Figure 16C:
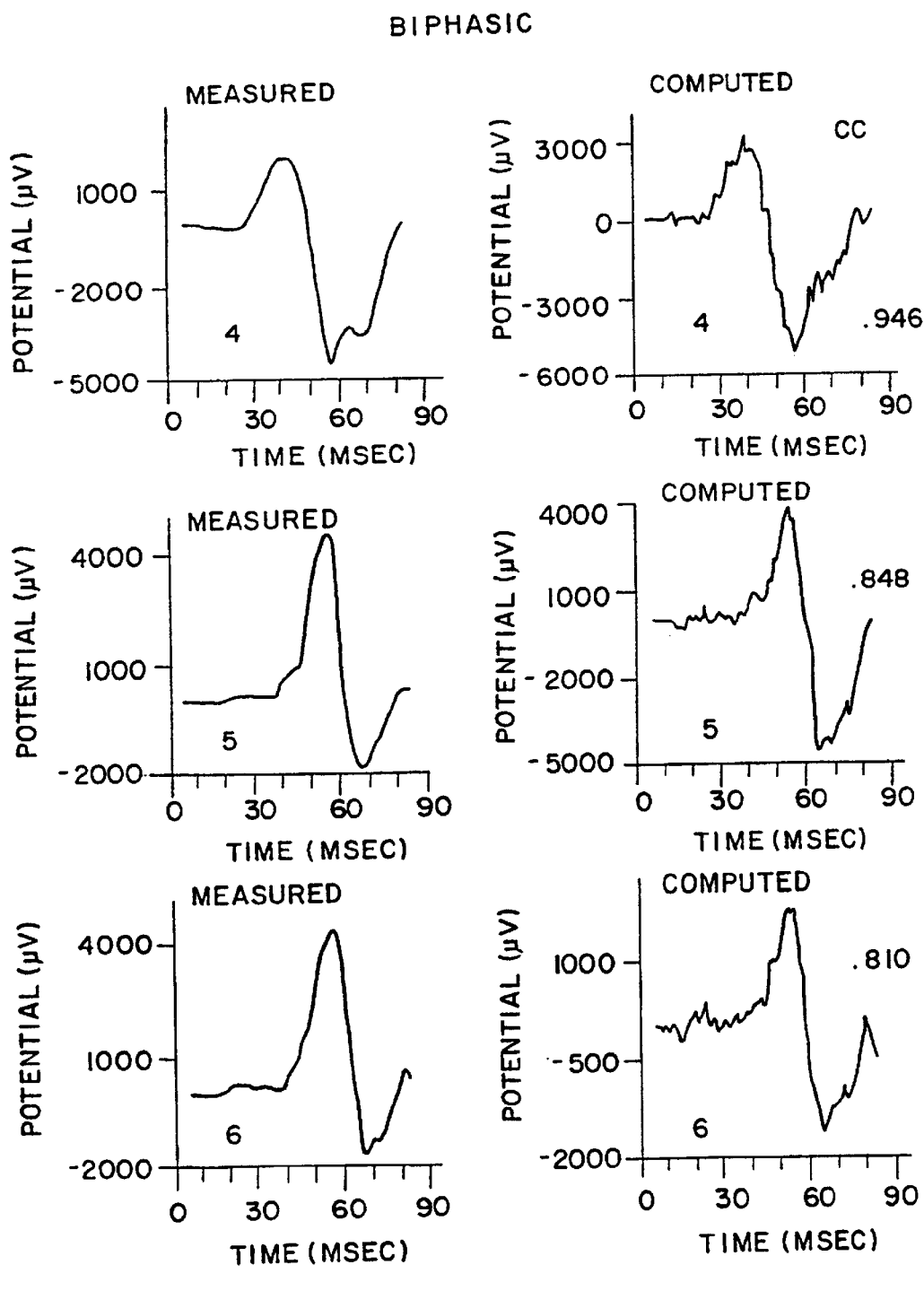
Figure 16D:
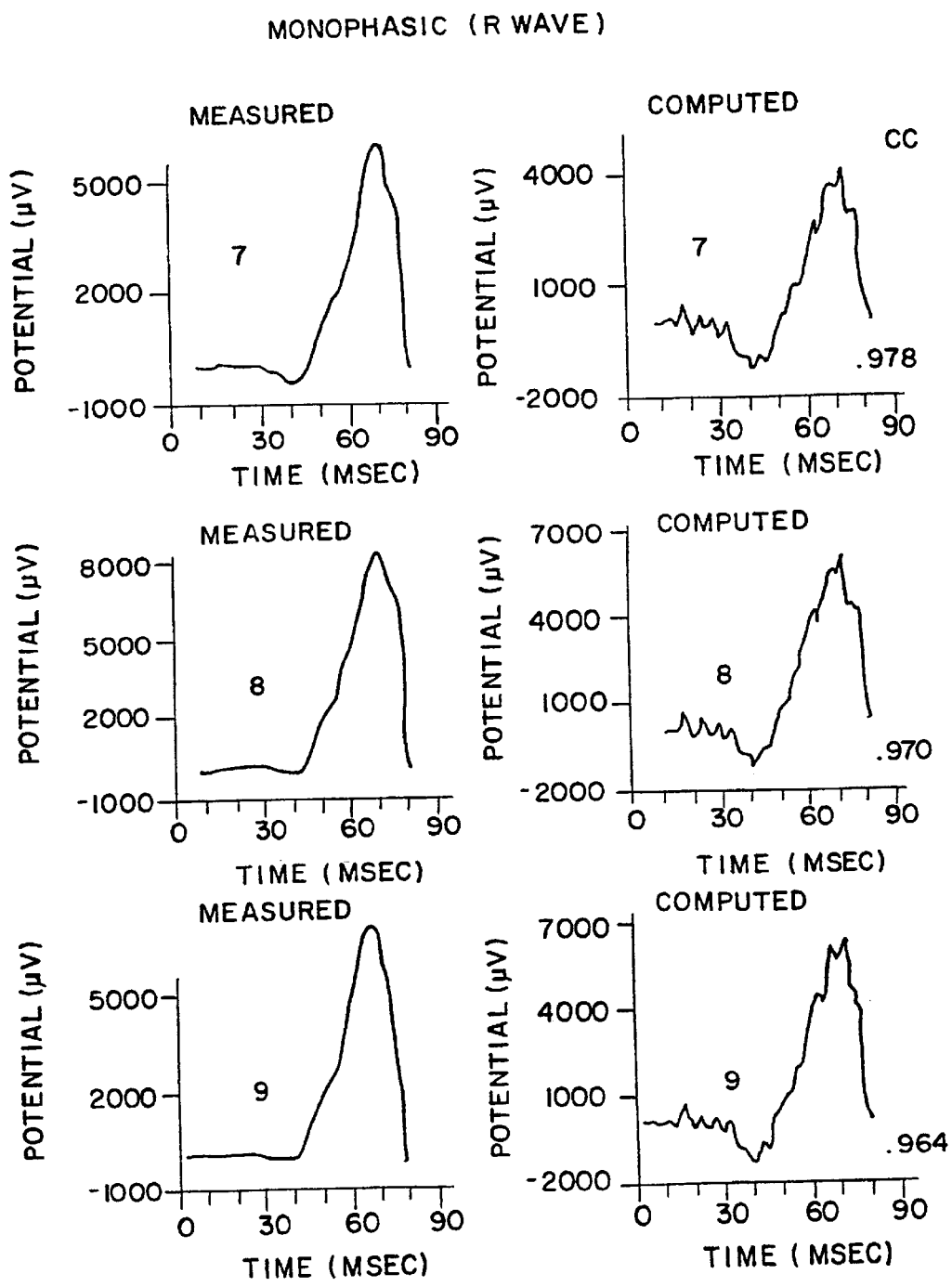

FIG. 13 shows potentials for the two middle pacing sites (sites #2 and #3). The torso potentials are not shown, and only the epicardial views that contain relevant information (anterior and left views) are shown. For pacing site #2, the inverse-reconstructed pacing site is located 10 mm from its measured location, and the reconstructed maxima are located 0 mm and 27 mm from their measured locations. The center of the ellipse of site #3 is reconstructed to its exact measured location; the maxima are reconstructed 18 mm and 28 mm from their respective measured locations.

FIG. 14 shows a summary of ECGI's ability to locate noninvasively the single pacing sites, positioned from anterior to posterolateral (again, only the anterior and left views are shown). In this figure, the epicardial mesh is shown instead of the contour plots, and only the pacing sites, identified by asterisks, are depicted. One can see that the progression of the pacing sites from anterior to posterolateral across the epicardium is reconstructed correctly in the noninvasively computed maps (bottom row; compare to measured sites in top row). The error in the location of the reconstructed pacing sites averages only 5 mm from their measured positions.

Multiple Pacing Sites:

Referring back to FIG. 11, Color Plate 2 shows the potential distributions for two simultaneous pacing site (#1 and #4). The measured epicardial potential maps (top row, right) show the two intense negative areas that reflect the two sites of early epicardial activation. The torso potential distribution looks very much like the superposition of the torso potential distribution from the individual pacing sites (plate 1 and FIG. 12), but notice that although the area of the minimum potential is broader in this figure than in color plate 1, there is only one minimum. Using the torso data to reconstruct the epicardial potentials (bottom row, right), however, both epicardial minima are reconstructed as approximate negative ellipses, and the position errors of their center points relative to the measured ones are 7 mm and 4 mm respectively.

Sites #1 and #4 are approximately 52 mm apart on the heart; the distance between their reflected minima on the effective epicardial envelope is approximately 65 mm. Sites #1 and #3 (anterior sites) are closer, at an intersite distance of approximately 35 mm on the heart and 40 mm on the envelope (color plate 3). The torso potentials look almost identical to those of the single pacing site in color plate 1. The reconstructed epicardial potentials, however, resolve both minima distinctly and in their exact locations. A more challenging test of the method is the two posterolateral pacing sites (#3 and #4), because they are located in a region of the heart that is farther from the chest wall, and also because the pacing sites are closer together (approximately 17 mm on the heart; 26 mm on the epicardial envelope). In FIG. 15, the noninvasively computed potentials reconstruct both posterolateral pacing sites distinctly. The error of position is approximately 5 mm and 4 mm for sites #3 and #4 respectively. Again, the body surface potentials only show one minimum, failing to reflect these two simultaneous pacing sites.

Epicardial Electrograms:

FIG. 16 demonstrates the noninvasive reconstruction of temporal epicardial unipolar electrograms. In FIG. 16A, the usual four views of the epicardial surface are shown. Sample electrograms are-displayed for sites (electrodes) close to (1, 2, and 3), partially away from (4, 5, and 6), and far away from (7, 8, and 9) the pacing site. In panels B, C, and D, both measured and computed electrograms are displayed. Three main types of waveforms—monophasic negative (FIG. 16B), biphasic (FIG. 16C), and monophasic positive (FIG. 16D)—are reconstructed. Notice the close resemblance of the noninvasively reconstructed electrograms as compared with the measured epicardial electrograms. The cross correlations (CC) for the plotted electrograms are printed in the figure and range from 0.810 to 0.998. Looking at the electrograms from the entire epicardial surface (not displayed), CC is greater than 0.9 for 72% of all epicardial electrodes (54% with CC>0.95). There are some outliers where the value of CC is poor, but CC is less than 0.5 in only 5% of the electrodes. In a number of the computed electrograms there are discontinuities of potential ("jagged" appearance) that do not exist in the measured electrograms. The reason for these discontinuities is that each time frame is computed with the quasi-static Tikhonov regularization scheme, in which each time frame is computed independent of all other time frames. In our procedure, we compute epicardial maps at discrete intervals of 1 msec. One would expect temporal discontinuities in the electrograms since they are constructed from discrete maps without the application of a temporal smoothing procedure.

Figure 17:
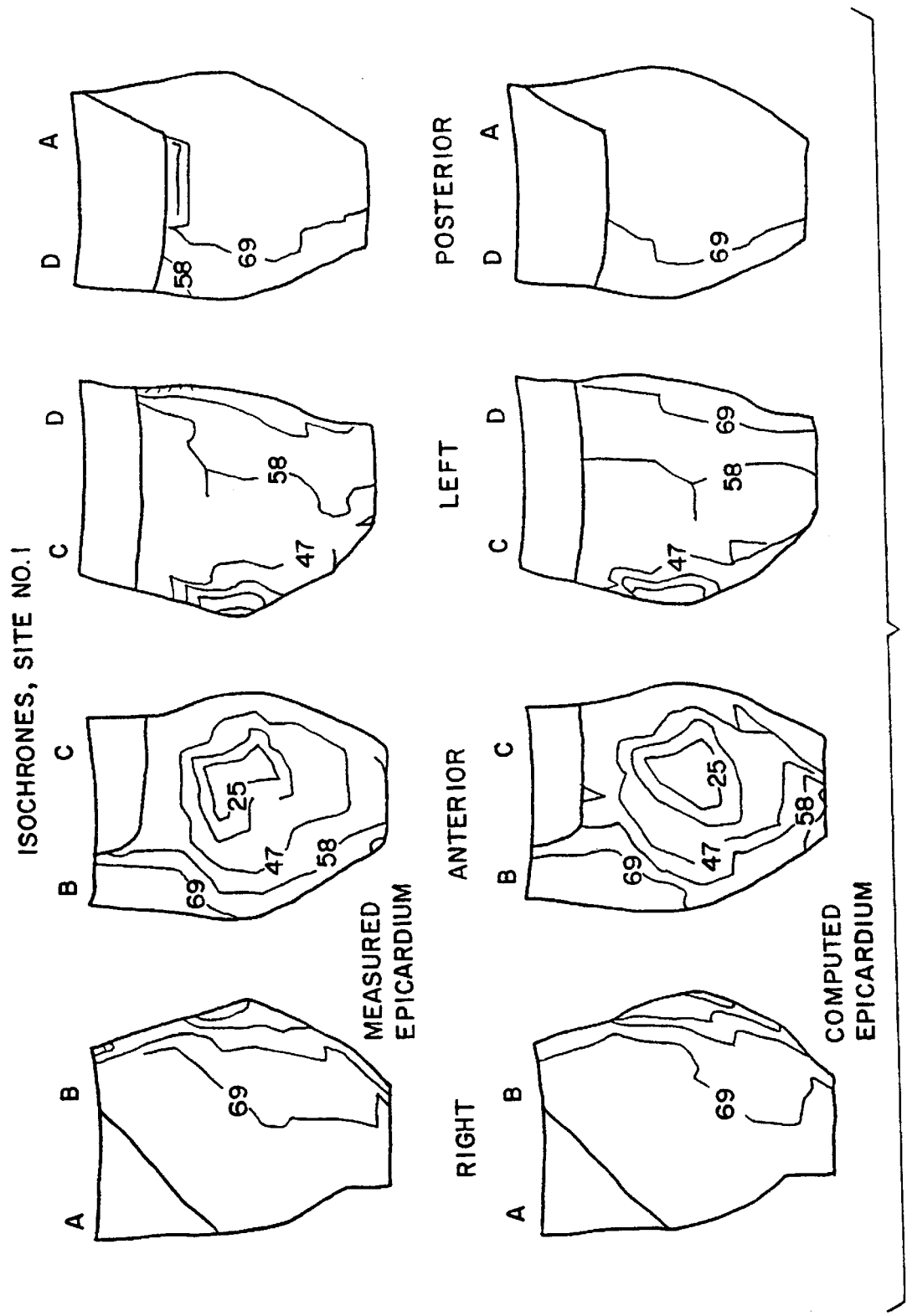
FIG. 17 shows measured and computed isochrones.

Epicardial Isochrones:

Isochrones were computed for both the measured and the noninvasively reconstructed epicardial potentials. FIG. 17 shows the isochrones for site #1. Notice that the regions of earliest activation are reproduced in the computed isochrones, matching the measured ones. Notice also, the spatial nonuniformities of isochrone density. In the measured isochrones there are regions with apparent faster spread of epicardial activation (right, left and posterior views, where the isochrones are sparse) and regions with relatively slow activation spread (where isochrones are crowded). For example, in the anterior view there is a region of relatively slow spread between 47 and 69 m-sec as evident by the crowding of isochrones in this area. Both the "fast" and "slow" areas are reproduced in the noninvasively computed isochrone map.

Figure 20:
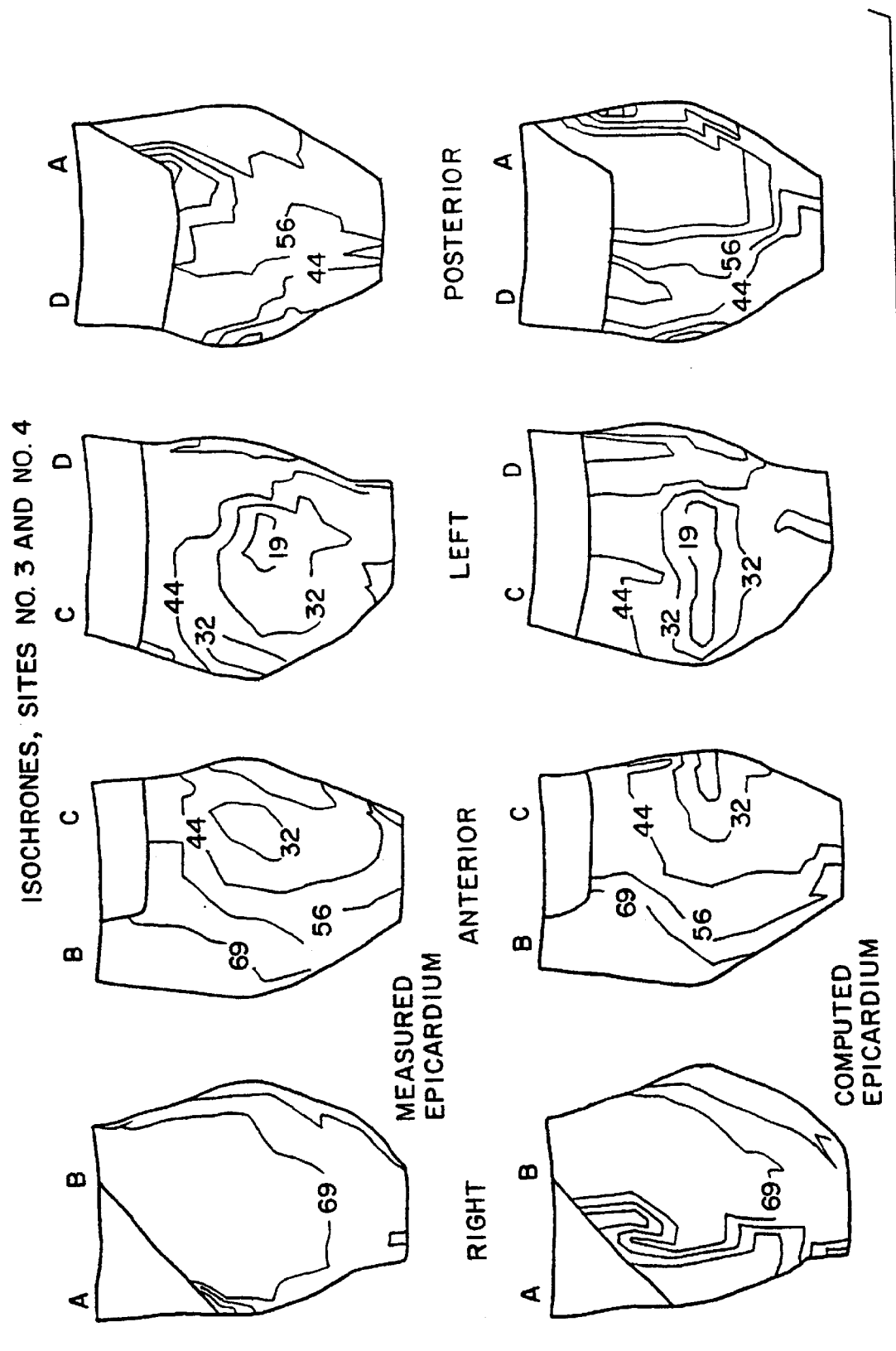
FIG. 20 shows measured and computed isochrones.

FIGS. 18, 19, and 20 show the activation sequences (isochrones) associated with the double pacing sites of color plates 2 and 3 and FIG. 15 respectively. Notice that in all three figures, the noninvasively reconstructed patterns of activation (epicardial isochrones) closely resemble the measured ones. In all but FIG. 20, two distinct sites of earliest ventricular activation are reconstructed. This is true for sites that are 52 mm or 35 mm apart; anterior or posterolateral. Even in FIG. 20 where the sites are posterolateral and only 17 mm apart, the first isochrone is elongate. This pattern implies a large region of earliest activation which is consistent with the presence of more than a single pacing site.

The results of this study demonstrate that Electrocardiographic Imaging (ECGI) is capable of noninvasively reconstructing epicardial potentials, temporal electrograms, and isochrones from potentials measured on the body surface with good accuracy and resolution. The study evaluates the ability to identify, locate and resolve single and multiple electrical events, as simulated by ventricular pacing. With anterior and posterolateral pacing, body surface potential mapping (BSPM) is able to detect the existence of an event taking place anteriorly or posterolaterally. Conventional ECG would show this as well, and the fact that the QRS is wide could help identify the rhythm as ventricular. However, even the BSPM is unable to identify, with acceptable accuracy, the location of the electrical event in the heart. Measured epicardial potentials reflect single or double pacing sites and identify their location with good accuracy. The inverse computations reconstruct these locations noninvasively with an error no worse than 10 mm. This result implies that the method is capable of reconstructing the location of arrhythogenic foci with this accuracy. Further evaluation is needed in the setting of actual ventricular tachycardias and in the presence of structural heart disease.

BSPM is also limited when trying to characterize the electrical activity of the heart for more than a single event. When two sites are paced, even as far apart as 52 mm, the torso potentials show only one minimum (see color plates 2 and 3 whose torso potential distributions for two pacing sites are very similar to that of color plate 1 for one pacing site). With ECGI, however, sites as close as 17 mm apart on the heart are reconstructed well and the individual sites are resolved (color plates 2 and 3, and FIG. 15). This is true for the anterior minima where the pacing sites are 19 mm and 26 mm, respectively, from the chest wall, and also for the posterior minima where the pacing sites are as far as 82 mm and 99 mm from the chest wall. This has specific clinical relevance when more than one electrical event is taking place simultaneously, especially if surgical or catheter ablation is indicated. It would then be imperative to know the number of regions of arrhythmogenic activity (e.g. two preexcitation sites) and exactly where they are. In a more general sense, simultaneous pacing from two sites at varying distances provides a measure of the ability of ECGI to resolve multiple electrical events. It also demonstrates its capability to reconstruct epicardial potentials, electrograms and isochrones for complex excitation patterns (i.e. in the presence of multiple, interacting wavefronts) that can typically be present during cardiac activation.

Because it is sometimes difficult to examine a long series of electric potential maps, especially in a clinical setting where time is of the essence, an isochronal map can be helpful. Although much of the valuable information present in the potential distribution is not preserved in the isochronal map, significant information about the entire activation sequence can be seen at one glance. Moreover, for epicardial pacing, the patterns of the isochrones like those of the potentials are related to the local fiber orientation (anisotropy) in that they tend to be quasi-elliptical with their major axis parallel to the fiber direction. The noninvasive isochronal maps correspond accurately to those computed directly from the measured potentials. The regions of earliest activation are located, and multiple pacing regions are resolved for sufficient intersite distance by the noninvasive reconstruction approach. In addition, spatial nonuniformities in the spread of spicardial activation (i.e. regions of sparse and regions of crowded isochrones) are identified. This is an important property of the reconstructed isochrones since in pathological conditions, crowding of isochrones indicates a region of slow conduction. An area of slow conduction is a key component of the reentry circuit in reentrant arrhythmias, and its localization could provide important mechanistic and diagnostic information.

The reconstruction of epicardial electrograms is important because it provides information on the temporal nature of activity in localized areas. An added benefit is that clinicians are accustomed to viewing and interpreting them. The results in FIG. 16 demonstrate the ability of ECGI and the inverse method to reconstruct noninvasively electrograms of either monophasic or biphasic waveforms with great accuracy. It is also from these leads that the time of activation are computed, providing high accuracy for the reconstruction of noninvasive isochrone maps.

This study concludes the ECGI is able to identify and locate, with good accuracy, single and multiple events by noninvasively computing the epicardial potential distribution from the body surface potentials. Specifically, this study demonstrates its ability to locate single and multiple pacing sites that simulate arrhythmogenic foci, suggesting its potential use in guiding interventional procedures (e.g. ablation). From a broader perspective, the results of this study suggest a wide array of possibilities for potential clinical and experimental application. Examples include: (1) The ability to map, simultaneously (during a single beat) and noninvasively, the electrical activity of the heart opens the door for mapping of nonsustained or dynamically changing arrhythmias (e.g. functional reentry circuits that, continually change or drifting spiral wave). Further research is needed to determine if epicardial potential patterns and isochrones can identify a common pathway of multiple reentry circuits during polymorphic VT and whether this information can be reconstructed by ECGI from body surface data. Such a common pathway constitutes a potential target for effective ablation of the tachycardia. (2) Spatial nonuniformities of epicardial activation spread (e.g. areas of sparse or crowded isochrones) can be located and mapped noninvasively with this technique. In pathological conditions, such nonuniformities might reflect nonuniformities of excitation spread that could play an important role in arrhythmogenesis. Our ability to recognize areas with variable density of isochrones in normal hearts sets the stage for further studies to determine whether slow conduction can also be detected during arrhythmic activity. Work in this direction has already begun in our laboratory. (3) The method could also be used to evaluate, in a given patient, the efficacy of antiarrhythmic drug therapy by noninvasively monitoring its effects on the spatial patterns of myocardial activation and recovery (e.g. whether it increases or decreases dispersion of repolarization). (4) Recently, the need for a noninvasive method for identifying patients at risk of sudden death has been emphasized. Empirical indices from body-surface ECG (T-wave alternans, dispersion of QT intervals) have been considered. The ability to "record" noninvasively from the heart itself will be very helpful in this regard by increasing detection sensitivity and by allowing one to relate these indices more directly to cardiac electrical activity. For example, QT dispersion is determined based on differences between individual leads on the body surface electrocardiogram. Since each surface lead reflects activity in the entire heart, this measure can not be related to actual spatial heterogeneity of repolarization in the heart itself, which is a recognized arrhythmogenic property. With ECGI one could obtain noninvasive information about the degree of spatial heterogeneity on the heart itself and locate the region that contributes to increased dispersion (and, therefore, to arrhythmogenesis). Similarly, alternans in the surface ECG could be related noninvasively to local beat-to-beat electrical changes in the heart. (5) Another example to potential clinical use is increased specificity of differentiating between types of arrhythmias. Recently, ECG indices (QT interval changes in response to Mexiletine or to an increase in heart rate) were shown to differentiate between two genetic types of the Long QT Syndrome, LQT3 and LQT2, each requiring different therapy. A related study showed that different genotypes of the long QT syndrome were associated with different phenotypic T-wave patterns on the ECG. In another study, two types of idiopathic VT were differentiated in terms of initiation sites based on body surface potential maps. It is highly probable that the specificity and ability to differentiate between arrhythmia types (especially important where the differential diagnosis is required for specific therapy) will be greatly enhanced by analyzing noninvasively reconstructed epicardial data rather than relying on body surface data alone.

Similar to the clinical usefulness of a noninvasive electrophysiologic imaging technique, one can envision its experimental potential. It could be used to study arrhythmias in the nonanaesthetized, intact animal under physiological conditions. Moreover, it could provide a noninvasive tool for studying arrhythmogenesis in patients with chronic heart disease that develops and persists over the course of many years, where the mechanism of arrhythmias and their properties might differ greatly from those in animal models.

Using the method and system described, the epicardial ECGI procedure has indeed been used in the clinical setting in human patients. Initial efforts focused on patient categories that provide an opportunity to evaluate and verify the inverse reconstruction. To this end, inverse reconstructions were performed for the following cases: (1) Patients with an implantable, epicardial lead cardioverter-defibrillator (ICD) during epicardial pacing; (2) Normal Sinus Rhythm (NSR); (3) Right Bundle Branch Block (RBBB); (4) Left Bundle Branch Block (LBBB). For all patients, BSPMs were obtained with the 224-electrode vest and mapping system. Heart-torso geometries were determined either from CT or using the digitizer/x-ray method. Specific information is provided below.

Noninvasive Reconstruction of Epicardial Potentials in Humans During Epicardial Pacing.

Reconstructions were performed in three patients during activation induced by epicardial stimulation (using two ICD epicardial electrodes spaced by 10–20 mm). Geometry, including epicardial pacing electrode positions, were determined by CT in two patients and using the digitizer/biplane x-ray in one patient. In all cases, reconstructed epicardial potentials were characterized by an early intense negative region (minimum) at the pacing site, as expected and consistent with the torso-tank data (FIGS. 11–15). Based on the early minimum, the pacing sites are located with an accuracy and resolution of about 10 mm (the actual position of the pacing electrodes is determined from the CT or x-ray reconstructions and provides the "gold standard"). This accuracy is a measure of the accuracy and resolution with which electrical events (e.g., arrhythmogenic foci) can be located noninvasively in the clinical setting. With time, the negative region spreads, reflecting the spread of activation away from the pacing site. During repolarization, the reconstructed epicardial potential pattern is very similar to that during depolarization, except that the polarity is reversed— an intense positive region replaces the minimum at the pacing site and spreads with time away from this site. This "mirror image" potential pattern is typical of a ventricular ectopic (or paced) beat that spreads slowly without involvement of the conduction system. Under such conditions, time of activation spread is much longer than differences in activation-recovery times (action potential durations) between different regions of the heart. Therefore, the sequence of repolarization is determined mostly by the sequence of depolarization, hence the "mirror image" potential pattern that is noninvasively reconstructed correctly by ECGI. An example is shown in FIG. 21.

I. Normal Sinus Rhythm.

BSPMs and geometrical information were obtained in 8 normal volunteers. The BSPMs are consistent with our large database of previously published maps during normal sinus rhythm. ECGI reconstructions of epicardial potentials, electrograms, and isochrones were performed and analyzed in 4 subjects. The noninvasively reconstructed epicardial potential map patterns and their time progression during QRS and T-wave, as well as the activation sequence, are consistent with those recorded experimentally directly from the epicardium in the human heart, in the canine, and in the chimpanzee. Importantly, cardiac electrophysiological events are successfully reconstructed, including the anterior potential minimum associated with right ventricular (RV) breakthrough, the fragmented positive region on the lateral left ventricle (LV) during mid-QRS (reflecting activation of this region), and migration of this positive region posteriorly and towards the LV base during late-QRS.

This ECGI capability, demonstrated here in human subjects, is consistent with our earlier NSR inverse reconstructions in the torso-tank preparation. FIG. 22 shows an example of noninvasive RV breakthrough reconstruction in a normal volunteer.

II. Right Bundle Branch Block (RBBB) and Left Bundle Branch Block (LBBB):

The patterns of ventricular activation in RBBB and in LBBB lend themselves to qualitative interpretation and evaluation since in these abnormalities the ventricles are activated sequentially (i.e., RV after LV in advanced RBBB, and LV after RV in LBBB) rather than simultaneously (the normal sequence with a fully intact conduction system). As we have shown in an earlier RBBB study, this sequential activation pattern is reflected in the BSPM. BSPM and geometrical data were obtained in 3 RBBB patients; ECGI reconstructions were performed in 1 out of the 3. BSPMs are consistent with those recorded during the earlier study. Initial analysis of reconstructed epicardial potentials demonstrate sequential activation (RV following LV) with absence of RV breakthrough and very long time of RV activation (no involvement of the conduction system). Data were also recorded from 4 LBBB patients and ECGI reconstructions were performed in 1. BSPMs are consistent with published data and with our database of 37 patients (unpublished). Initial analysis of reconstructed epicardial potential maps shows fast activation of RV followed by slower activation of LV. The reconstructed patterns for RBBB and LBBB are consistent with epicardial patterns recorded in humans and in experimental animals.

The above description merely provides a disclosure of particular embodiments of the invention and is not intended for the purpose of limiting the same thereto. As such, the invention is not limited to only the above described embodiments. Rather, it is recognized that one skilled in the art could conceive alternative embodiments that fall within the scope of the invention.

Having thus described the invention, we hereby claim:

1. A method for noninvasively determining electrical activity on a surface of a heart of a living being, the being having a torso with an exposed body surface surrounding the heart, the method comprising steps of:

determining electrical potentials at a plurality of locations on the body surface of the being by monitoring electrodes that are positioned to detect electrical potentials at the plurality of locations;

repeating the determining at predetermined intervals over a predetermined period of time;

generating body surface potential maps that represent a distribution of the electrical potentials determined over the predetermined period of time;

determining an epicardial envelope surrounding the heart;

determining a geometry of the torso of the being;

determining locations of the electrodes;

determining a position of the heart within the torso;

determining a matrix of transformation using a boundary element method based on the epicardial envelope, the geometry, the locations of the electrodes and the position of the heart within the torso;

regularizing the matrix of transformation;

determining an electrical potential distribution over the surface of the heart based on the regularized matrix of transformation and the body surface potential map.

2. The method as set forth in claim 1 wherein the electrodes are disposed on a vest that is worn by the being.

3. The method as set forth in claim 1 wherein the determining of the epicardial envelope, geometry of the torso, the location of the electrodes and the position of the heart includes conducting a CT scan.

4. The method as set forth in claim 1 wherein the determining of the epicardial envelope, the geometry of the torso and the position of the heart includes conducting a biplane x-ray procedure.

5. The method as set forth in claim 4 wherein the determining of the location of the electrodes includes implementing a digitizer.

6. The method as set forth in claim 1 wherein the determining of the electrical potential distribution over the surface of the heart includes operating with the regularized matrix of transformation on the body surface potential map.

7. The method as set forth in claim 1 further comprising generating electrograms based on the electrical potential distribution.

8. The method as set forth in claim 7 further comprising generating isochrones based on a derivative of the electrograms.

9. A system for noninvasively determining electrical activity on a surface of a heart of a human being, the human being having a torso with an exposed body surface surrounding the heart, the system comprising:

electrode means for simultaneously determining electrical potentials at a plurality of locations on the body surface of the human being at predetermined intervals over a predetermined period to of time, the electrode means comprising a plurality of electrodes disposed in a vest adapted to be positioned on the torso;

means for generating a body surface potential map that represents a distribution of the electrical potentials determined over the predetermined period of time;

means for determining a geometry of the torso of the human being;

means for determining locations of the electrodes;

means for determining a position of the heart within the torso;

means for determining an epicardial envelope of the heart;

means for determining a matrix of transformation based on the geometry, the locations of the electrodes and the position of the heart within the torso;

means for regularizing the matrix of transformation;

means for determining an electrical potential distribution over the surface of the heart based on the regularized matrix of transformation and the body surface potential map.

10. A system for noninvasively determining electrical activity on a surface of a heart of a human being, the human being having a torso with an exposed body surface surrounding the heart, the system comprising:

a vest having a plurality of electrodes disposed therein for determining electrical potentials at a plurality of locations on the body surface of the human being at predetermined intervals over a predetermined period of time, the electrodes being positionable to detect electrical potentials at the plurality of locations;

means for generating body surface potential maps that represent a distribution of the electrical potentials determined over the predetermined period of time;

an imaging device to determine an epicardial envelope of the heart, a geometry of the torso of the human being, locations of the electrodes, and a position of the heart within the torso;

means for determining a matrix of transformation based on the geometry, the locations of the electrodes and the position of the heart within the torso;

means for regularizing the matrix of transformation; and, means for determining an electrical potential distribution over the surface of the heart based on the regularized matrix of transformation and the body surface potential map.

11. A system for noninvasively determining electrical activity on a surface of a heart of a human being, the human being having a torso with an exposed body surface surrounding the heart, the system comprising:

a vest having a plurality of electrodes disposed therein for determining electrical potentials at a plurality of locations on the body surface of the human being at predetermined intervals over a predetermined period of time, the electrodes being positionable to detect electrical potentials at the plurality of locations;

means for generating a body surface potential map that represents a distribution of the electrical potentials determined over the predetermined period of time;

an imaging device to determine a geometry of the torso of the human being and a position of the heart within the torso;

a digitizer to determine locations of the electrodes relative to the torso;

means for determining a matrix of transformation based on the geometry, the locations of the electrodes and the position of the heart within the torso;

means for regularizing the matrix of transformation; and, means for determining an electrical potential distribution over the surface of the heart based on the regularized matrix of transformation and the body surface potential map.

12. The system as set forth in claim 9 wherein the means for determining the electrical potential distribution includes means for multiplying the regularized matrix of transformation by the body surface potential map.

13. A system for noninvasively determining electrical activity on a surface of a heart of a human being, the human being having a torso with an exposed body surface surrounding the heart, the system comprising:

a plurality of electrodes positioned to determine electrical potentials at a plurality of locations on the body surface of the human being at predetermined intervals over a predetermined period of time;

means for generating body surface potential maps that represent a distribution of the electrical potentials determined over the predetermined period of time;

an imaging device to determine an epicardial envelope of the heart, a geometry of the torso of the human being, locations of the electrodes, and a position of the heart within the torso;

means for determining a matrix of transformation based on the geometry, the locations of the electrodes and the position of the heart within the torso;

means for regularizing the matrix of transformation; and, means for determining an electrical potential distribution over the surface of the heart based on the regularized matrix of transformation and the body surface potential map.

14. The system as set forth in claim 13 further comprising a vest having the plurality of electrodes disposed therein.

15. A system for noninvasively determining electrical activity on a surface of a heart of a human being, the human being having a torso with an exposed body surface surrounding the heart, the system comprising:

a plurality of electrodes positioned to determine electrical potentials at a plurality of locations on the body surface of the human being at predetermined intervals over a predetermined period of time;

means for generating a body surface potential map that represents a distribution of the electrical potentials determined over the predetermined period of time;

an imaging device to determine a geometry of the torso of the human being and a position of the heart within the torso;

a digitizer to determine locations of the electrodes relative to the torso;

means for determining a matrix of transformation based on the geometry, the locations of the electrodes and the position of the heart within the torso;

means for regularizing the matrix of transformation; and, means for determining an electrical potential distribution over the surface of the heart based on the regularized matrix of transformation and the body surface potential map.

16. The system as set forth in claim 15 wherein the means for determining the electrical potential distribution includes means for multiplying the regularized matrix of transformation by the body surface potential map.

17. The system as set forth in claim 15 further comprising a vest having the plurality of electrodes disposed therein.

* * * * *